(12) United States Patent
Khanna

(10) Patent No.: US 9,782,491 B2
(45) Date of Patent: *Oct. 10, 2017

(54) PEPTIDE CONJUGATES FOR TREATING PAIN

(71) Applicant: INDIANA UNIVERSITY RESEARCH AND TECHNOLOGY CORPORATION, Indianapolis, IN (US)

(72) Inventor: Rajesh Khanna, Indianapolis, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 181 days.

This patent is subject to a terminal disclaimer.

(21) Appl. No.: 14/405,324

(22) PCT Filed: Jun. 4, 2013

(86) PCT No.: PCT/US2013/043977
§ 371 (c)(1),
(2) Date: Dec. 3, 2014

(87) PCT Pub. No.: WO2013/184614
PCT Pub. Date: Dec. 12, 2013

(65) Prior Publication Data
US 2015/0151000 A1    Jun. 4, 2015

Related U.S. Application Data

(60) Provisional application No. 61/655,380, filed on Jun. 4, 2012.

(51) Int. Cl.
| | | |
|---|---|---|
| *A61K 38/10* | (2006.01) | |
| *A61K 38/16* | (2006.01) | |
| *C07K 14/435* | (2006.01) | |
| *A61K 47/48* | (2006.01) | |
| *C07K 14/47* | (2006.01) | |
| *C07K 14/705* | (2006.01) | |
| *C07K 14/00* | (2006.01) | |
| *A61K 38/00* | (2006.01) | |

(52) U.S. Cl.
CPC ........ *A61K 47/48246* (2013.01); *C07K 14/00* (2013.01); *C07K 14/4702* (2013.01); *C07K 14/705* (2013.01); *A61K 38/00* (2013.01); *C07K 2319/10* (2013.01); *C07K 2319/70* (2013.01); *C07K 2319/74* (2013.01)

(58) Field of Classification Search
None
See application file for complete search history.

(56) References Cited

U.S. PATENT DOCUMENTS

2002/0127198 A1    9/2002    Rothbard et al.
2008/0279864 A1    11/2008    Yue et al.

FOREIGN PATENT DOCUMENTS

WO    2012009075 A1    1/2012

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
PCT International Search Report and Written Opinion completed by the ISA/US on Jan. 3, 2014 and issued in connection with PCT/US2013/043977.
Piekarz, et al. "CRMP-2 Mediated Decrease of High and Low Voltage-Activated Calcium Channels, Attenuation of Nocicoeptor Excitability, and Anti-Nociception in a Model of AIDS-Therapy Induced Painful Peripheral Neuropathy" Molecular Pain. Jul. 24, 2012. vol. 8; pp. 1-19; abstract; col. 2, p. 3; paragraph 2, col. 2, page: paragraph 1, col. 2, p. 12; paragraph 1.
Zamponi, G. et al., (2009) *Brain Res. Rev.*, 60, 84-89.
Snutch, T. P. (2005) *NeuroRx.*, 2, 662-670.
Malmberg, A. B. and Yaksh, T. L. (1994) *J. Neurosci.*, 14, 4882-4890.
Bowersox, S. S., et al., (1996) *J. Pharmacol. Exp. Ther.*, 279, 1243-1249.
Souza, A. H., et al., (2008) *Pain*, 140, 115-126.
McGivern, J. G. (2007) *Neuropsychiatr. Dis. Treat.*, 3, 69-85.
Schmidtko, A. et al., (2010) Lancet., 375, 1569-1577.
Bowersox, S. S., et al., (1992) J Cardiovasc. Pharmacol., 20, 756-764.
Brittain, J. M., et al., (2009) *J. Biol. Chem.*, 284, 31375-31390.
Brittain, J. M. et al., (2011) *Nat. Med.*, 17, 822-829.
Wilson, S. M., et al., (2011) *Channels (Austin.* ), 5, 449-456.
Ripsch, M. S., et al., (2012) *Translational Neuroscience*, 3, 1-8.
Bucci, G., et al., (2011) *J Physiol.*, 589, 3085-3101.
Mochida, S., et al., (1996) *Neuron*, 17, 781-788.
Pragnell, M., et al., (1994) *Nature*, 368, 67-70.
DeWaard M., et al., (1997) *Nature*, 385, 446-450.
Li, B., et al., (2004) *Mol. Pharmacol.*, 66, 761-769.
Lee, A., et al., (1999) *Nature*, 399, 155-159.
Peterson, B. Z., et al., (1999) *Neuro*, 22, 549-558.
Zuhlke, R. D., et al., (1999) *Nature*, 399, 159-162.
Qin, N., et al., (1999) *Proc. Natl. Acad. Sci. U. S. A.*, 96, 2435-2438.
Van, P. F., et al., (2004) *Nature*, 429, 671-675.
Tedford, H. et al., (2010) *Mol. Brain.*, 3, 6, 7 pages.
Frank, R. (2002) *J Immunol. Methods*, 267, 13-26.
Chan, A. W., et al., (2007) *Channels (Austin.* ),1, 11-20.
Wienken, C. J., et al., (2010) *Nat. Commun.*, 1, 100, 7 pages.
van den Bogaart, G., et al., (2012) J Biol. Chem., 11, 16447-53.
Wang, Y. and Khanna, R. (2011) *Transl. Neurosci.*, 2, 13-22.
Wang, Y., et al., (2010) *J. Biol. Chem.*, 285, 25296-25307.

(Continued)

*Primary Examiner* — Christine J Saoud
*Assistant Examiner* — Jon M Lockard
(74) *Attorney, Agent, or Firm* — Barnes & Thornburg LLP

(57) ABSTRACT

Described herein are compounds, composition, and methods for treating pain. In particular, described herein compounds, compositions, and methods that modulate the protein-protein-interaction between CRMP-2 and a calcium channel for treating pain.

17 Claims, 8 Drawing Sheets

(56) References Cited

OTHER PUBLICATIONS

Brittain, J., et al., (2012) *Channels (Austin)*, 6, 94-102.
Brittain, J. M., et al., (2011) *J. Biol. Chem.*, 286, 37778-37792.
Chi, X. X., et al., (2009) *J. Cell Sci.*, 23, 4351-4362.
Jacks, T., et al., (1994) *Nat. Genet.*, 7, 353-361.
Hingtgen, C. M., et al., (2006) *Neuroscience*, 137, 637-645.
Wang, Y., et al., (2010) *Translational Neuroscience*, 1, 106-114.
Chen, J. J., et al., (1996) *Peptides*, 17, 31-37.
Joseph, E. K., et al., (2004) *Pain*, 107, 147-158.
Zillner, K., et al., (2012) *Methods Mol. Biol.*, 815:241-52, 241-252.
Sheng, Z. H., et al., (1994) *Neuron*, 13, 1303-1313.
Patrakitkomjorn, S., et al.,. (2008) *J. Biol. Chem*, 283, 9399-9413.
Van, P. F. and Minor, D. L., Jr. (2006) *Biochem. Soc. Trans*, 34, 887-893.
Qin, N., et al., (1997) *Proc. Natl. Acad. Sci. U. S. A.*, 94, 8866-8871.
Bell, T. J., et al., (2004) *Neuron*, 41, 127-138.
Altier, C., Dale, et al., (2007) *J. Neurosci.*, 27, 6363-6373.
Winquist, R. J., et al., (2005) *Biochem. Pharmacol.*, 70, 489-499.
Cizkova, D., et al., (2002) *Exp. Brain Res.*, 147, 456-463.
Saegusa, H., et al., (2001) *EMBO J.*, 20, 2349-2356.
Vanegas, H. and Schaible, H. (2000) *Pain*, 85, 9-18.
Neugebauer, V., et al., (1996) *J. Neurophysiol.*, 76, 3740-3749.
Sluka, K. A. (1997) *Pain*, 71, 157-164.
Neugebauer, V., et al., (1996) *Neuroscience*, 71, 1095-1109.
Fossat, P., et al., (2010) *J Neurosci.*, 20, 1073-1085.
Favereaux, A., et al., (2011) *EMBO J.*, 30, 3830-3841.
Pavlidis, P. and Noble, W. S. (2003) *Bioinformatics*, 19, 295-296.
White, D. M. and Cousins, M. J. (1998) *Brain Res.*, 801, 50-58.

* cited by examiner

PEPTIDE CONJUGATES FOR TREATING PAIN

CROSS-REFERENCE TO RELATED APPLICATIONS

This application is a national stage entry under 35 U.S.C. §371(b) of International Application Serial No. PCT/US2013/043977, filed Jun. 4, 2013, which claims the benefit of U.S. Provisional Application No. 61/655,380, filed Jun. 4, 2012, the entire disclosures of which are expressly incorporated by reference in their entirety.

INCORPORATION BY REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jun. 3, 2013, is named 29920-225459_SL.txt and is 55,096 bytes in size.

TECHNICAL FIELD

The invention described herein pertains to the treatment of pain. In particular, the invention described herein pertains to compounds, compositions, and methods that modulate the protein-protein-interaction between CRMP-2 and a calcium channel.

BACKGROUND AND SUMMARY OF THE INVENTION

Despite a variety of available analgesics, treatment of chronic pain remains a large unmet medical need. Although some chronic pain conditions may be treated adequately by existing drugs, many patients fail to achieve adequate pain relief. This is especially the case for patients suffering from neuropathic pain due to trauma, disease, and/or neurotoxic anti-retroviral pain, which are often unresponsive to conventional analgesics. Furthermore, the chronic use of many analgesics is limited by side effects or by the development of tolerance. In 2010, analgesics accounted for sales of $22 Billion globally and $13 Billion in the US (1. I. Melnikova, Nat. Rev. Drug Discov. 9, 589 (2010); 2. C. Harstall, Pain Clinical Updates X, 1 (2003)). The highest selling analgesics were opiates, followed by non-steroidal anti-inflammatory drugs (NSAIDs), antiepileptics, antidepressants, and local anesthetics.

The N-type voltage-gated calcium channel (CaV2.2) is a nidus for neurotransmitter release and transmission of nociception. However, it has been reported that the use of CaV2.2 blockers in pain therapeutics is limited by side-effects resulting from inhibition of the physiological functions of CaV2.2 within the CNS. The N-type voltage-gated calcium channel (CaV2.2) has recently gained immense popularity as one of the key factors in the ascending pain pathway (see reviews by Zamponi and Snutch (1,2)). As such, it is believed herein that regulation of CaV2.2 expression and function is posed to have a major impact on the presentation of multiple pain states. Inhibition of CaV2.2 by synthetic conopeptides has been reported to provide analgesic relief in a variety of platforms (3-6). However, given the importance of CaV2.2 integrity in peripheral and central synapses, directly targeting channel function is reportedly complicated by a myriad of adverse side effects (7-9). The use of calcium channel peptides as decoys to disrupt binding of regulatory proteins has previously been demonstrated using the II-III cytoplasmic loop (14) and the alpha interaction domain (AID) of CaV2.2 (15). Intracellular injection of a peptide containing the II-III loop, containing the synprint interaction site, prevented association of the CaV2.2 with the synaptic core complex, reducing synaptic transmission (15). Peptides containing the AID domain of CaV2.2 prevented G-protein-mediated inhibition of channel function by disrupting binding of the Gβγ subunit to the channel (14). Alternatives for existing therapies are needed.

It has been discovered herein that disruption of collapsin response mediator protein 2 (CRMP2) and N-type voltage-gated calcium channel (CaV2.2) protein-protein interaction is anti-nociceptive for both inflammatory and neuropathic pain. Described herein are compounds and pharmaceutical compositions for treating pain. Also described herein are uses of the compounds and pharmaceutical compositions described herein for treating pain, and methods for treating pain using the compounds and pharmaceutical compositions described herein.

In one embodiment, peptide inhibitors of the CRMP2-CaV2.2 protein-protein interaction, based on and derived from CRMP2, such as CBD3, and related peptides are useful in treating inflammatory and neuropathic pain. Without being bound by theory, it is believed herein that such peptide inhibitors, by perturbing interactions with the neuromodulator CRMP2, contribute to suppression of neuronal hypersensitivity and nociception. It is appreciated herein that CRMP2 is a protein capable of binding to and enhancing CaV2.2 activity. Using a peptide tiling array, novel peptides were identified that bind CRMP2. Illustrative of such peptides include those within the first intracellular loop (CaV2.2 [388-402] 'L1') and the carboxyl terminus (CaV1.2[2014-2028] 'Ct-dis'), each of which bind CRMP2. Microscale thermophoresis demonstrates micromolar and nanomolar binding affinities between recombinant CRMP2 and synthetic L1 and Ct-dis peptides, respectively. Co-immunoprecipitation experiments show that CRMP2 association with CaV2.2 is inhibited such L1 and Ct-dis peptides. L1 and Ct-dis, rendered cell penetrant by fusion with carrier proteins, such as but not limited to the protein transduction domain of the HIV TAT protein, are evaluated in in vitro and in vivo experiments. Depolarization-induced calcium influx in dorsal root ganglion (DRG) neurons is inhibited by the peptides described herein. The Ct-dis peptides strongly inhibits depolarization-stimulated release of the neuropeptide transmitter calcitonin gene-related peptide (CGRP) in mouse DRG neurons. Similar results are obtained in DRGs from mice with a heterozygous mutation of Nf1 linked to neurofibromatosis type 1. Ct-dis peptide, illustratively administered intraperitoneally, exhibits antinociception in Zalcitabine (2'-3'-dideoxycytidine (ddC)) model of AIDS therapy-induced peripheral neuropathy.

Without being bound by theory, it is believed herein that targeting protein-protein interactions which regulate CaV2.2 may provide similar analgesic benefits as direct inhibition while avoiding complications associated with channel block. Described herein are peptides derived from channel domains demonstrated to coordinate CRMP2 that target the reciprocal interface of the interaction.

In another embodiment, described herein are 15 amino acid length peptides derived from the I-II cytoplasmic loop and the distal C-terminus of CaV2.2 and CaV1.2, respectively. The peptides effectively disrupt the interaction between CRMP2 and CaV2.2, reducing calcium influx. These channel regions are known to coordinate interactions between the channel and many other regulatory proteins.

The I-II cytoplasmic loop contains interaction sites for CaVβ proteins (16) as well as Gβγ subunits (17). Additionally, the carboxyl terminus also contains interaction sites for Gβγ subunits (18). Calmodulin has also been shown to interact with this region (19-22). However, the illustrative 15 amino acid peptides described herein do not overlap with the binding sites for calmodulin or the Gβγ subunits (23,24), but there is partial overlap of the L1 peptide with the carboxyl terminal portion of the AID, which is responsible for binding CaVβ.

In another embodiment, the peptides described herein are useful in treating mechanical hyperalgesia associated with HIV retroviral treatment-induced neuropathy when administered systemically. For example, systemic administration of Ct-dis peptide transiently reverses mechanical hyperalgesia associated with HIV retroviral treatment-induced neuropathy.

In another embodiment, pharmaceutical compositions containing one or more of the compounds are also described herein. In one aspect, the compositions include a therapeutically effective amount of the one or more compounds for treating a patient with pain. It is to be understood that the compositions may include other component and/or ingredients, including, but not limited to, other therapeutically active compounds, and/or one or more carriers, diluents, excipients, and the like. In another embodiment, methods for using the compounds and pharmaceutical compositions for treating patients with pain are also described herein. In one aspect, the methods include the step of administering one or more of the compounds and/or compositions described herein to a patient with pain. In another aspect, the methods include administering a therapeutically effective amount of the one or more compounds and/or compositions described herein for treating patients with pain. In another embodiment, uses of the compounds and compositions in the manufacture of a medicament for treating patients with pain are also described herein. In one aspect, the medicaments include a therapeutically effective amount of the one or more compounds and/or compositions for treating a patient with pain.

It is to be understood herein that the compounds described herein may be used alone or in combination with other compounds useful for treating pain, including those compounds that may be therapeutically effective by the same or different modes of action. In addition, it is to be understood herein that the compounds described herein may be used in combination with other compounds that are administered to treat other symptoms of pain.

DETAILED DESCRIPTION

Figure 1:
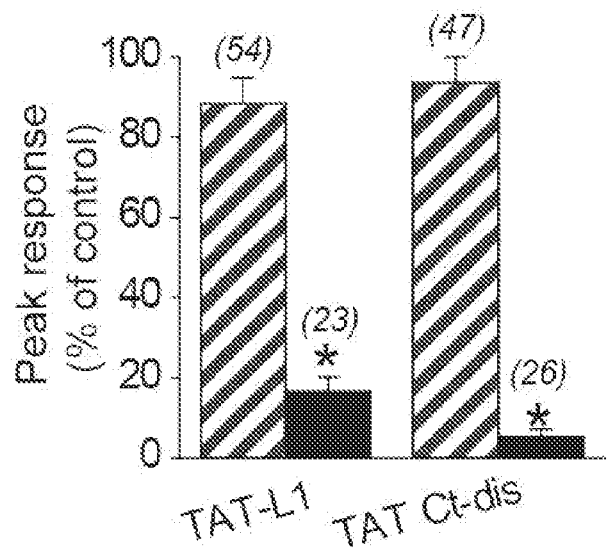
FIG. 1 shows a bar graph of the peak fluorescence response (adjusted for background) of DRGs incubated for 20 min with 3 µM TaT-L1 or TAT-Ct-dis peptides (hashed bars) 30 µM TaT-L1 or TAT-Ct-dis peptides (solid bars) as a percentage compared to untreated DRGs. Normalized values represent the average±SEM from three separate imaging experiments, with the number of cells per condition indicated in parentheses. Asterisks indicate statistical significance compared with untreated cells ($p<0.05$, one-way ANOVA followed by Dunnett's post-hoc test).

In one embodiment, peptides and peptide conjugates are described herein for treating pain. In another embodiment, the peptides are fragments, or addition, deletion or mutation sequences from the CaV-binding domain. In another embodiment, the peptides are fragments, or addition, deletion or mutation sequences from the CaV-binding domain 3. In another embodiment, the peptides are addition, deletion or mutation sequences of CaV-binding domain 3 (CBD3) peptide.

In another embodiment, the peptide conjugates are fusion peptides or proteins of the peptides described herein and carrier proteins or peptides, cargo proteins or peptides, transport proteins or peptides, or cell permeating proteins or peptides. Illustrative carrier proteins and peptides, cargo proteins and peptides, transport proteins and peptides, and cell permeating proteins and peptides include, but are not limited to TAT, TATm, PTD, PTR, pVEC, SynB, R9 (SEQ ID NO: 1), R9-TAT ("R9" disclosed as SEQ ID NO: 1), MTS, PreS.sub.2-TLM, HTLV-II REX, MAP, TP, PEP, and PrP Also described herein are peptide inhibitors that are capable of inhibiting a protein-protein-interaction between CRMP-2 and a calcium channel.

Also described herein are peptide conjugates of the peptide inhibitors described herein that are capable of inhibiting a protein-protein-interaction between CRMP-2 and a calcium channel.

In another embodiment, the peptide inhibitor is the human L1 peptide or fragment thereof, such as the human L1 peptide corresponding to amino acids 386-404 or 388-402, found in any of CaV1.2 (L), CaV2.1 (P/Q), CaV2.3 (R), or CaV2.2 (N). Illustratively, the peptide inhibitor is the human calcium channel peptide or fragment thereof the sequence comprising YXXWIXXAEXXXXXX (SEQ ID NO: 124), where X is an optionally substituted amino acid, YLEWIFKAEEVMLAE (SEQ ID NO: 125), YMEWISKAEEVILAE (SEQ ID NO: 146), YRAWIDKAEEVMLAE (SEQ ID NO: 150), or YLDWITQAEDIDPEN (SEQ ID NO: 151). In another embodiment, the peptide inhibitor comprises YLEWIFKAEEVMLAE (SEQ ID NO: 125).

In another embodiment, the peptide inhibitor is a human Ct-Dis peptide or fragment thereof, such as the human Ct-Dis peptide corresponding to the rat Ct-Dis peptide 2014-2028 found in any of CaV1.2 (L), CaV2.1 (P/Q), CaV2.3 (R), or CaV2.2 (N). Illustratively, the peptide inhibitor is the human calcium channel peptide or fragment thereof corresponding to the rat Ct-Dis peptide of the sequence comprising NSSXXXXXXXXXXXX (SEQ ID NO: 126), where X is an optionally substituted amino acid, NSSFPSIHCSSWSEE (SEQ ID NO: 127), NSSPVHFAE (SEQ ID NO: 152), PRRPAA (SEQ ID NO: 153), or MRHTGGISPPPDG (SEQ ID NO: 154). In another embodiment, the peptide inhibitor comprises the human sequence corresponding to the rat Ct-Dis peptide of the sequence comprising NSSFPSIHCSSWSEE (SEQ ID NO: 127).

Several illustrative embodiments of the invention are described by the following enumerated clauses:

1. A peptide conjugate of the formula

T-A or a pharmaceutically acceptable salt thereof, wherein T is a carrier protein or peptide, and A is peptide inhibitor capable of inhibiting a protein-protein-interaction between CRMP-2 and a calcium channel.

2. The conjugate of clause 1 wherein where the carrier protein or peptide is a transport peptide or cell penetrating peptide.

3. The conjugate of any one of the preceding clauses wherein the calcium channel is CaV2.2.

4. The conjugate of any one of the preceding clauses wherein T is selected from the group consisting of TAT, TATm, PTD, PTR, pVEC, SynB, R9 (SEQ ID NO: 1), R9-TAT ("R9" disclosed as SEQ ID NO: 1), MTS, PreS$_2$-TLM, HTLV-II REX, MAP, TP, PEP, and PrP.

5. The conjugate of any one of the preceding clauses wherein T is TAT or TATm.

6. The conjugate of any one of the preceding clauses wherein T is TAT.

7. The conjugate of any one of the preceding clauses wherein T is R9 (SEQ ID NO: 1) or R9-TAT("R9" disclosed as SEQ ID NO: 1).

8. The conjugate of any one of the preceding clauses wherein T is R9 (SEQ ID NO: 1).

9. The conjugate of any one of the preceding clauses wherein A is a peptide comprising YXXWIXXAEXXXXXX (SEQ ID NO: 124), where X is an optionally substituted amino acid.

10. The conjugate of any one of the preceding clauses wherein A is a peptide comprising YLEWIFKAEEVMLAE (SEQ ID NO: 125), YMEWISKAEEVILAE (SEQ ID NO: 149), YRAWIDKAEEVMLAE (SEQ ID NO: 150), or YLDWITQAEDIDPEN (SEQ ID NO: 151).

11. The conjugate of any one of the preceding clauses wherein A is a peptide comprising YLEWIFKAEEVMLAE (SEQ ID NO: 125).

12. The conjugate of any one of the preceding clauses wherein A is a peptide comprising the human calcium channel peptide or fragment thereof corresponding to the rat Ct-Dis peptide of the sequence comprising NSSXXXXXXXXXXXX (SEQ ID NO: 126), where X is an optionally substituted amino acid, NSSFPSIHCSSWSEE (SEQ ID NO: 127), NSSPVHFAE (SEQ ID NO: 152), PRRPAA (SEQ ID NO: 153), or MRHTGGISPPPDG (SEQ ID NO: 154).

13. The conjugate of any one of the preceding clauses wherein A is a peptide comprising the human calcium channel peptide or fragment thereof corresponding to the rat Ct-Dis peptide of the sequence comprising NSSFPSIHCSSWSEE (SEQ ID NO: 127).

14. The conjugate of any one of the preceding clauses wherein A is a CBD fragment, or an addition, deletion of mutation sequence thereof.

15. The conjugate of any one of the preceding clauses wherein A is a CBD fragment, or an addition, deletion of mutation sequence thereof comprising ARSR (SEQ ID NO: 128).

16. The conjugate of any one of the preceding clauses wherein A is a CBD fragment, or an addition, deletion of mutation sequence thereof comprising ARSRL (SEQ ID NO: 129).

17. The conjugate of any one of the preceding clauses wherein A is a CBD fragment, or an addition, deletion of mutation sequence thereof comprising ARSRLA (SEQ ID NO: 14).

18. The conjugate of any one of the preceding clauses wherein A is a CBD3, or an addition, deletion of mutation sequence thereof.

19. The conjugate of any one of the preceding clauses wherein A is a CBD3, or an addition, deletion of mutation sequence thereof comprising ARSR (SEQ ID NO: 128).

20. The conjugate of any one of the preceding clauses wherein A is a CBD3, or an addition, deletion of mutation sequence thereof comprising ARSRL (SEQ ID NO: 129).

21. The conjugate of any one of the preceding clauses wherein A is a CBD3, or an addition, deletion of mutation sequence thereof comprising ARSRLA (SEQ ID NO: 14).

22. The conjugate of any one of the preceding clauses wherein A is a peptide comprising ARSR (SEQ ID NO: 128).

23. The conjugate of any one of the preceding clauses wherein A is a peptide comprising ARSRL (SEQ ID NO: 129).

24. The conjugate of any one of the preceding clauses wherein A is a peptide comprising ARSRLA (SEQ ID NO: 14).

25. The conjugate of any one of the preceding clauses wherein A is a peptide comprising ARSRLX (SEQ ID NO: 130).

26. The conjugate of any one of the preceding clauses wherein A is a peptide comprising ARSRLK (SEQ ID NO: 131).

27. The conjugate of any one of the preceding clauses wherein A is a peptide comprising ARSRXXXXL (SEQ ID NO: 132), where X is an optionally substituted amino acid.

28. The conjugate of any one of the preceding clauses wherein A is a peptide comprising ARSRLXXXL (SEQ ID NO: 133), where X is an optionally substituted amino acid.

29. The conjugate of any one of the preceding clauses wherein A is a peptide comprising ARSRLAXXL (SEQ ID NO: 134), where X is an optionally substituted amino acid.

30. The conjugate of any one of the preceding clauses wherein A is a peptide comprising ARSRXXXXXXVP (SEQ ID NO: 135), where X is an optionally substituted amino acid.

31. The conjugate of any one of the preceding clauses wherein A is a peptide comprising ARSRLXXXXXVP (SEQ ID NO: 136), where X is an optionally substituted amino acid.

32. The conjugate of any one of the preceding clauses wherein A is a peptide comprising ARSRLAXXXXVP (SEQ ID NO: 137), where X is an optionally substituted amino acid.

33. The conjugate of any one of the preceding clauses wherein A is a peptide comprising ARSRXXXXXXVPR (SEQ ID NO: 138), where X is an optionally substituted amino acid.

34. The conjugate of any one of the preceding clauses wherein A is a peptide comprising ARSRLXXXXXVPR (SEQ ID NO: 139), where X is an optionally substituted amino acid.

35. The conjugate of any one of the preceding clauses wherein A is a peptide comprising ARSRLAXXXXVPR (SEQ ID NO: 140), where X is an optionally substituted amino acid.

36. The conjugate of any one of the preceding clauses wherein A is a peptide comprising ARSRXXXXXXXXF (SEQ ID NO: 141), where X is an optionally substituted amino acid.

37. The conjugate of any one of the preceding clauses wherein A is a peptide comprising ARSRLXXXXXXXF (SEQ ID NO: 142), where X is an optionally substituted amino acid.

38. The conjugate of any one of the preceding clauses wherein A is a peptide comprising ARSRLAXXXXXXF (SEQ ID NO: 143), where X is an optionally substituted amino acid.

39. The conjugate of any one of the preceding clauses wherein A is a peptide comprising ARSRXXXXXXVPRXL (SEQ ID NO: 144), where X is an optionally substituted amino acid.

40. The conjugate of any one of the preceding clauses wherein A is a peptide comprising ARSRLXXXXXVPRXL (SEQ ID NO: 145), where X is an optionally substituted amino acid.

41. The conjugate of any one of the preceding clauses wherein A is a peptide comprising ARSRLAXXXXVPRXL (SEQ ID NO: 146), where X is an optionally substituted amino acid.

42. The conjugate of any one of the preceding clauses wherein A is a peptide comprising ARSRXXXLXG (SEQ ID NO: 147), where X is an optionally substituted amino acid.

43. The conjugate of any one of the preceding clauses wherein A is a peptide comprising ARSRLXXLXG (SEQ ID NO: 148), where X is an optionally substituted amino acid.

44. The conjugate of any one of the preceding clauses wherein A is a peptide comprising ARSRLAXLXG (SEQ ID NO: 123), where X is an optionally substituted amino acid.

45. The conjugate of any one of the preceding clauses wherein in each instance X is an amino acid.

46. The conjugate of any one of the preceding clauses wherein in each instance X is a naturally occurring amino acid.

47. The conjugate of any one of the preceding clauses wherein T-A is amidated on the C-terminus. 48. The conjugate of any one of the preceding clauses wherein T-A is acylated on the N-terminus.

49. The conjugate of any one of the preceding clauses wherein T-A is acetylated on the N-terminus.

50. A pharmaceutical composition comprising one or more of the conjugates of any one of the preceding clauses, and one or more carriers, diluents, or excipients, or a combination thereof.

51. A conjugate or pharmaceutical composition of any one of the preceding clauses for treating pain in a host animal.

52. Use of the conjugate or pharmaceutical composition of any one of the preceding clauses in the manufacture of a medicament for treating pain in a host animal.

53. A method for treating pain in a host animal, the method comprising the step of administering to the host animal a therapeutically effective amount of the conjugate or pharmaceutical composition of any one of clauses 1 to 51.

54. The conjugate, pharmaceutical composition, use, or method of any one of the preceding clauses wherein the host animal is a human.

55. The conjugate, pharmaceutical composition, use, or method of any one of the preceding clauses wherein the pain is pain associated with trauma.

56. The conjugate, pharmaceutical composition, use, or method of any one of the preceding clauses wherein the pain is neuropathic pain.

57. The conjugate, pharmaceutical composition, use, or method of any one of the preceding clauses wherein the pain is comorbid with diabetes.

58. The conjugate, pharmaceutical composition, use, or method of any one of the preceding clauses wherein the pain is diabetic neuropathy.

59. The conjugate, pharmaceutical composition, use, or method of any one of the preceding clauses wherein the pain is pain associated with therapy 60. The conjugate, pharmaceutical composition, use, or method of any one of the preceding clauses wherein the pain is pain associated with HIV treatment.

In another embodiment, the compound is a prodrug of the peptide inhibitor or carrier protein or peptide conjugate thereof.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl,β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl)pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, (C$_3$-C$_{20}$)alkanoyl; halo-(C$_3$-C$_{20}$)alkanoyl; (C$_3$-C$_{20}$)alkenoyl; (C$_4$-C$_7$)cycloalkanoyl; (C$_3$-C$_6$)-cycloalkyl(C$_2$-C$_{16}$)alkanoyl; optionally substituted aroyl, such as unsubstituted aroyl or aroyl substituted by 1 to 3 substituents selected from the group consisting of halogen, cyano, trifluoromethanesulphonyloxy, (C$_1$-C$_3$)alkyl and (C$_1$-C$_3$)alkoxy, each of which is optionally further substituted with one or more of 1 to 3 halogen atoms; optionally substituted aryl(C$_2$-C$_{16}$)alkanoyl and optionally substituted heteroaryl(C$_2$-C$_{16}$)alkanoyl, such as the aryl or heteroaryl radical being unsubstituted or substituted by 1 to 3 substituents selected from the group consisting of halogen, (C$_1$-C$_3$)alkyl and (C$_1$-C$_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, (C$_1$-C$_3$)alkyl, and (C$_1$-C$_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

In addition to the illustrative dosages and dosing protocols described herein, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and/or vehicles.

It to be understood herein that peptide inhibitors will generally have improved pharmacokinetic behavior when conjugated to a carrier peptide or protein, such as a cargo protein or peptide, a transport peptide or peptide, or a cell penetrating protein or peptide (CPP). Illustrative improved pharmacokinetic behavior includes longer serum and/or circulating half-lives, and/or greater cell permeation. Illustratively, the peptide inhibitors are conjugated with a transport peptide or cell penetrating peptide selected from the group consisting of TAT, TATm, PTD, PTR (also referred to as PTD), pVEC, SynB, R9 (SEQ ID NO: 1), R9-TAT ("R9" disclosed as SEQ ID NO: 1), MTS, PreS.sub.2-TLM, HTLV-II REX, MAP, TP, PEP, and PrP. Illustratively, the peptide inhibitors are conjugated with TAT, the model amphipathic peptide (MAP), or membrane translocating sequence of k-FGF (MTS) to provide longer half-lives, such as half-lives in human serum of >72 h and 48 h, respectively. Illustratively, the peptide inhibitors are conjugated with oligoarginines (R9) (SEQ ID NO: 1) to provide greater cell permeability, such as, for example, 100-fold greater penetration than TAT (Wender et al., Proc. Natl. Acad. Sci. U.S.A. 97, 13003 (2000)).

It to be further understood herein that peptide inhibitors will generally have improved pharmacokinetic behavior when stabilized, such as by selective site mutations, or chemical modification. Illustratively, peptide inhibitors, and conjugates thereof, are stabilized by acetylation, amidation, or cyclization.

Without being bound by theory, it is believed herein that the efficacy of targeting VGCC regulation in alleviating pain behavior validates the importance of the calcium channel in pain signaling. Highly expressed on nociceptive fibers and within the dorsal horn of the spinal cord, CaV2.2 plays a fundamental role in relaying pain signals from the periphery. Alternative splice variants found on small diameter nociceptive neurons are associated with increased thermal and mechanical hyperalgesia (44,45). CaV2.2 is believed to be responsible for increased neurotransmitter release commonly associated with chronic and neuropathic pain conditions (1,2,46,47). Consistent with the role of CaV2.2 in pain signaling, genetic deletion, as well as pharmacologic block of CaV2.2, impairs nociceptive processing (3,48). Additionally, central blockade of CaV2.2 is effective in treating some cases of chronic pain which have been intractable to other interventions (8).

While the N-type channel appears to predominate in neuropathic pain conditions, the L-type channel also reportedly plays a role in acute and inflammatory pain signaling (49). Without being bound by theory, as CRMP2 interacts with CaV1.2 as well as CaV2.2, it is believed herein that TAT-Ct-dis is interrupting binding between CRMP2 and both N- and L-type channels. The ability to simultaneously target both interactions may aid in its efficacy. Pharmacologic block of L-type channels reduces acute response to noxious peripheral stimuli (50). Administration of the L-type blocker, Nifedipine, into the dorsal horn of the spinal cord prevented secondary thermal and mechanical hyperalgesia following injection of capsaicin into the hindpaw (51). Without being bound by theory, it is believed herein that the L-type channel also plays a role in inflammatory-mediated pain signaling. Spinal block of L-type channels attenuates the enhanced response of primary afferents to noxious and innocuous stimuli during inflammation-induced central sensitization (52). Consequently, intrathecal administration of Nifedipine reduces late-phase nociceptive behavior following formalin administration (3). A recent report attributes the maintenance of chronic neuropathic pain (spinal nerve ligation model) to CaV1.2 (53). Favereaux and colleagues also reported bi-directional regulation of CaV1.2 by a single microRNA, thus implicating CaV1.2 as a novel possible therapeutic target in neuropathic chronic pain (54). The complementary roles of these two calcium channels in both peripheral and spinal processing of pain signaling indicate opportunities for therapeutic intervention through control of their regulation. Without being bound by theory, it is believed herein that CRMP2 may regulate either or both channels in the modulation of pain signaling. Subsequently, by binding and sequestering CRMP2, the peptides and peptide conjugates described herein, including TAT-Ct-dis, may simultaneously affect N-type and L-type channel function.

The effective use of the compounds, compositions, and methods described herein for treating or ameliorating pain using one or more compounds described herein may be based upon animal models, such as murine, canine, porcine, and non-human primate animal models of disease. For example, it is understood that various forms of pain in humans may be characterized by a loss of function, and/or the development of symptoms, each of which may be elicited in animals, such as mice, rats, and other surrogate test animals. In particular the mouse and rat models of diabetic neuropathy (DN), HIV-associated distal symmetrical polyneuropathy (DSP) and chronic compression of the dorsal root ganglion (CCD) may be used to evaluate the methods of treatment and the pharmaceutical compositions described herein to determine the therapeutically effective amounts described herein.

The following examples further illustrate specific embodiments of the invention; however, the following illustrative examples should not be interpreted in any way to limit the invention.

EXAMPLES

Compound Examples

EXAMPLE. Materials. TAT-control peptide YGRK-KRRQRRR-WEAKEMLYFEALVIE (SEQ ID NO: 2), which is a random sequence with no homology to any known sequence; TAT-L1 YGRKKRRQRRR-YLEWIF-KAEEVMLAE (SEQ ID NO: 3); and TAT-Ct-dis YGRK-KRRQRRR-NSSFPSIHCSSSWSEE (SEQ ID NO: 4) were synthesized and HPLC-purified by Antagene Inc. (Sunnyvale, Calif.). All chemicals, unless noted are available from Sigma (St. Louis, Mo.). Lipofectamine 2000 is available from Invitrogen (Carlsbad, Calif.). Fura-2 AM is available from Teflabs (Austin, Tex.). Antibodies are available as follows: anti-CRMP2 polyclonal antibody, anti-syntaxin monoclonal antibody, and mouse anti-Flag M2 monoclonal antibody (Sigma, St. Louis, Mo.) and anti-CaV1.2 monoclonal antibody (UC Davis Neuromab, Davis, Calif.). The CRMP2-His-pET28B cDNA was provided by Dr. Rihe Liu (University of North Carolina) and the CRMP2-3xFlag construct was provided by Dr. Akihiro Kurimasa (Tottori University, Tottori, Japan). The peptide blot was synthesized at the SNRI core facility.

EXAMPLE. The following peptide inhibitors of the formula A are described, and may be prepared using conventional processes.

| Peptide (A) | Sequence | SEQ ID NO: |
|---|---|---|
| CBD3 | ARSRLAELRGVPRGL | 5 |
| CBD3$_{A6K}$ | ARSRLKELRGVPRGL | 6 |
| CBD3$_{R9L}$ | ARSRLAELLPRGL | 7 |
| CBD3$_{A6KR9L}$ | ARSRLKELLGVPRGL | 8 |
| CBD3$_{R9K}$ | ARSRLAELKGVPRGL | 9 |
| CBD3$_{A6KR9K}$ | ARSRLKELKGVPRGL | 10 |
| CBD3$_{G14F}$ | ARSRLAELRGVPRFL | 11 |
| CBD3$_{A6KG14F}$ | ARSRLKELRGVPRFL | 12 |
| CBD3$_{amidated}$ | ARSRLAELRGVPRGL | 13 |
| CBD3$_{□7-15}$ | ARSRLA | 14 |
| CBD3$_{□7-15A6K}$ | ARSRLK | 131 |
| L1 (CaV2.2) | YLEWIFKAEEVMLAE | 125 |
| L1 (CaV2.1) | YMEWISKAEEVILAE | 149 |
| L1 (CaV2.3) | YRAWIDKAEEVMLAE | 150 |
| L1 (CaV1.2) | YLDWITQAEDIDPEN | 151 |
| Ct-Dis (CaV1.2 (L)) | NSSFPSIHCSSWSEE | 127 |
| Ct-Dis (CaV2.1 (P/Q)) | NSSPVHFAE | 152 |
| Ct-Dis (CaV2.3 (R)) | PRRPAA | 153 |
| Ct-Dis (CaV2.2 (N)) | MRHTGGISPPPDG | 154 |

EXAMPLE. The following peptide conjugates of the formula T-A are described, and may be prepared using conventional processes, where T is a carrier protein or peptide, such as cargo protein or peptide, transport protein or peptide, or cell permeating protein or peptide; and A is a peptide inhibitor, as described herein.

| Peptide Conjugate (T-A) | Sequence | SEQ ID NO: |
|---|---|---|
| T-CBD3 | T-ARSRLAELRGVPRGL | 5 |
| T-CBD3$_{A6K}$ | T-ARSRLKELRGVPRGL | 6 |
| T-CBD3$_{R9L}$ | T-ARSRLAELLPRGL | 7 |
| T-CBD3$_{A6KR9L}$ | T-ARSRLKELLGVPRGL | 8 |
| T-CBD3$_{A6KR9K}$ | T-ARSRLKELKGVPRGL | 10 |
| T-CBD3$_{G14F}$ | T-ARSRLAELRGVPRFL | 11 |

| Peptide Conjugate (T-A) | Sequence | SEQ ID NO: |
|---|---|---|
| T-CBD3$_{A6KG14F}$ | T-ARSRLKELRGVPRFL | 12 |
| T-CBD3$_{amidated}$ (a) | T-ARSRLAELRGVPRGL | 13 |
| T-CBD3$_{T-acetylated}$ (b) | T-ARSRLAELRGVPRGL | 5 |
| T-CBD3$_{□7-15}$ | T-ARSRLA | 14 |
| T-CBD3$_{□7-15A6K}$ | T-ARSRLK | 131 |
| T-L1 (CaV2.2) | T-YLEWIFKAEEVMLAE | 125 |
| T-L1 (CaV2.1) | T-YMEWISKAEEVILAE | 149 |
| T-L1 (CaV2.3) | T-YRAWIDKAEEVMLAE | 150 |
| T-L1 (CaV1.2) | T-YLDWITQAEDIDPEN | 151 |
| T-Ct-Dis (CaV1.2 (L)) | T-NSSFPSIHCSSWSEE | 127 |
| T-Ct-Dis (CaV2.1 (P/Q)) | T-NSSPVHFAE | 152 |
| T-Ct-Dis (CaV2.3 (R)) | T-PRRPAA | 153 |
| T-Ct-Dis (CaV2.2 (N)) | T-MRHTGGISPPPDG | 154 |

(a) The C-terminal amino acid is amidated;
(b) The N-terminal amino acid is acetylated.

In the foregoing table, T is illustratively independently selected in each instance from TAT, TATm, PTD, PTR, pVEC, SynB, R9 (SEQ ID NO: 1), R9-TAT ("R9" disclosed as SEQ ID NO: 1), MTS, PreS.sub.2-TLM, HTLV-II REX, MAP, TP, PEP, and PrP.

EXAMPLE. The following peptide conjugates of the formula T-A are described, and may be prepared using conventional processes.

| Peptide Conjugate (T-A) | Sequence | SEQ ID NO: |
|---|---|---|
| TAT-CBD3 (ST1-104) | YGRKKRRQRRRARSRLAELRGVPRGL | 15 |
| TAT-CBD3$_{A6K}$ (ST1-105) | YGRKKRRQRRRARSRLKELRGVPRGL | 16 |
| TAT-CBD3$_{R9L}$ (ST1-106) | YGRKKRRQRRRARSRLAELLGVPRGL | 17 |
| TAT-GBD3$_{R9K}$ | YGRKKRRQRRRARSRLAELKGVPRGL | 18 |
| TAT-GBD3$_{G14F}$ (ST1-107) | YGRKKRRQRRRARSRLAELRGVPRFL | 19 |
| TAT-GB D3$_{A6KG14F}$ | YGRKKRRQRRRARSRLKELRGVPRFL | 20 |
| TAT-GBD2$_{amidated}$ (ST7-204) | YGRKKRRQRRRARSRLAELRGVPRGL | 21 |
| TAT-CBD2$_{acetylated}$ (ST7-304) | YGRKKRRQRRRARSRLAELRGVPRGL | 22 |
| TAT-CBD3$_{□7-15}$ (ST1-504) | YGRKKRRQRRRARSRLA | 23 |
| TATm-CBD3 | GRKKRRQRRRPPQARSRLAELRGVPRGL | 24 |
| TATm-GBD3$_{A6K}$ | GRKKRRQRRRPPQARSRLKELRGVPRGL | 25 |
| TATm-CBD3$_{R9L}$ | GRKKRRQRRRPPQARSRLAELLGVPRGL | 26 |
| TATm-CBD3$_{G14F}$ | GRKKRRQRRRPPQARSRLAELRGVPRFL | 27 |
| TATm-CBD3$_{amidated}$ | GRKKRRQRRRPPQARSRLAELRGVPRGL | 28 |
| TATm-CBD3$_{acetylated}$ | GRKKRRQRRRPPQARSRLAELRGVPRGL | 29 |
| TATm-CBD3$_{□7-15}$ | GRKKRRQRRRPPQARSRLA | 30 |
| PTD-CBD3 | RQIKIWFQNRRMKWKKARSRLAELRGVPRGL | 31 |
| PTD-GBD3$_{A6K}$ | RQIKIWFQNRRMKWKKARSRLKELRGVPRGL | 32 |
| PTD-CBD3$_{R9L}$ | RQIKIWFQNRRMKWKKARSRLAELLGVPRGL | 33 |
| PTD-CBD3$_{G14F}$ | RQIKIWFQNRRMKWKKARSRLAELRGVPRFL | 34 |
| PTD-CBD3$_{amidated}$ | RQIKIWFQNRRMKWKKARSRLAELRGVPRGL | 35 |
| PTD-CBD3$_{acetylated}$ | RQIKIWFQNRRMKWKKARSRLAELRGVPRGL | 36 |
| PTD-CBD3$_{□7-15}$ | RQIKIWFQNRRMKWKKARSRLA | 37 |
| pVEC-CBD3 | LLIILRRRIRKQAHAHSKARSRLAELRGVPRGL | 38 |
| pVEC-CBD3$_{A6K}$ | LLIILRRRIRKQAHAHSKARSRLKELRGVPRGL | 39 |
| pVEC-CBD3$_{R9L}$ | LLIILRRRIRKQAHAHSKARSRLAELLGVPRGL | 40 |

-continued

| Peptide Conjugate (T-A) | Sequence | SEQ ID NO: |
|---|---|---|
| pVEC-CBD3$_{G14F}$ | LLIILRRRIRKQAHAHSKARSRLAELRGVPRFL | 41 |
| pVEC-CBD3$_{amidated}$ | LLIILRRRIRKQAHAHSKARSRLAELRGVPRGL | 42 |
| pVEC-CBD3$_{acetylated}$ | LLIILRRRIRKQAHAHSKARSRLAELRGVPRGL | 43 |
| pVEC-CBD3$_{□7-15}$ | LLIILRRRIRKQAHAHSKARSRLA | 44 |
| SynB-CBD3 | RGGRLSYSRRRFSTSTGRARSRLAELRGVPRGL | 45 |
| SynB-CBD3$_{A6K}$ | RGGRLSYSRRRFSTSTGRARSRLKELRGVPRGL | 46 |
| SynB-CBD3$_{R9L}$ | RGGRLSYSRRRFSTSTGRARSRLAELLGVPRGL | 47 |
| SynB-CBD3$_{G14F}$ | RGGRLSYSRRRFSTSTGRARSRLAELRGVPRFL | 48 |
| SynB-CBD3$_{amidated}$ | RGGRLSYSRRRFSTSTGRARSRLAELRGVPRGL | 49 |
| SynB-CBD3$_{acetylated}$ | RGGRLSYSRRRFSTSTGRARSRLAELRGVPRGL | 50 |
| SynB-CBD3$_{□7-15}$ | RGGRLSYSRRRFSTSTGRARSRLA | 51 |
| R9-CBD3 (ST2-104) "(R9" disclosed as SEQ ID NO: 1) | RRRRRRRRRARSRLAELRGVPRGL | 52 |
| R9-CBD3$_{A6K}$ (ST2-104) "(R9" disclosed as SEQ ID NO: 1) | RRRRRRRRRARSRLKELRGVPRGL | 53 |
| R9-CBD3$_{R9L}$ (ST2-104) "(R9" disclosed as SEQ ID NO: 1) | RRRRRRRRRARSRLAELLGVPRGL | 54 |
| R9-CBD3$_{G14F}$ (ST2-104) "(R9" disclosed as SEQ ID NO: 1) | RRRRRRRRRARSRLAELRGVPRFL | 55 |
| R9-CBD3$_{amidated}$ (ST2-104) "(R9" disclosed as SEQ ID NO: 1) | RRRRRRRRRARSRLAELRGVPRGL | 56 |
| R9-CBD3$_{acetylated}$ (ST2-104) "(R9" disclosed as SEQ ID NO: 1) | RRRRRRRRRARSRLAELRGVPRGL | 57 |
| R9-CBD3$_{□7-15}$ (ST2-104) "(R9" disclosed as SEQ ID NO: 1) | RRRRRRRRRARSRLA | 58 |
| R9-TAT-CBD3 "(R9" disclosed as SEQ ID NO: 1) | GRRRRRRRRRPPQARSRLAELRGVPRGL | 59 |
| R9-TAT-CBD3$_{A6K}$ "(R9" disclosed as SEQ ID NO: 1) | GRRRRRRRRRPPQARSRLKELRGVPRGL | 60 |
| R9-TAT-CBD3$_{R9L}$ "(R9" disclosed as SEQ ID NO: 1) | GRRRRRRRRRPPQARSRLAELLGVPRGL | 61 |
| R9-TAT-CBD3$_{G14F}$ "(R9" disclosed as SEQ ID NO: 1) | GRRRRRRRRRPPQARSRLAELRGVPRFL | 62 |
| R9-TAT-CBD3$_{amidated}$ "(R9" disclosed as SEQ ID NO: 1) | GRRRRRRRRRPPQARSRLAELRGVPRGL | 63 |
| R9-TAT-CBD3$_{acetylated}$ "(R9" disclosed as SEQ ID NO: 1) | GRRRRRRRRRPPQARSRLAELRGVPRGL | 64 |
| R9-TAT-CBD3$_{□7-15}$ "(R9" disclosed as SEQ ID NO: 1) | GRRRRRRRRRPPQARSRLA | 65 |
| MTS-CBD3 (ST5-104) | AAVALLPAVLLALLAPARSRLAELRGVPRGL | 66 |
| MTS-CBD3$_{A6K}$ | AAVALLPAVLLALLAPARSRLKELRGVPRGL | 67 |
| MTS-CBD3$_{R9L}$ | AAVALLPAVLLALLAPARSRLAELLGVPRGL | 68 |
| MTS-CBD3$_{G14G}$ | AAVALLPAVLLALLAPARSRLAELRGVPRFL | 69 |
| MTS-CBD3$_{amidated}$ | AAVALLPAVLLALLAPARSRLAELRGVPRGL | 70 |
| MTS-CBD3$_{acetylated}$ | AAVALLPAVLLALLAPARSRLAELRGVPRGL | 71 |
| MTS-CBD3$_{□7-15}$ | AAVALLPAVLLALLAPARSRLA | 72 |

-continued

| Peptide Conjugate (T-A) | Sequence | SEQ ID NO: |
|---|---|---|
| PreS$_2$-TLM-CBD3 | PLSSIFSRIGDPARSRLAELRGVPRGL | 73 |
| PreS$_2$-TLM-CBD3$_{A6K}$ | PLSSIFSRIGDPARSRLKELRGVPRGL | 74 |
| PreS$_2$-TLM-CBD3$_{R9L}$ | PLSSIFSRIGDPARSRLAELLGVPRGL | 75 |
| PreS$_2$-TLM-CBD3$_{G14F}$ | PLSSIFSRIGDPARSRLAELRGVPRFL | 76 |
| PreS$_2$-TLM-CBD3$_{amidated}$ | PLSSIFSRIGDPARSRLAELRGVPRGL | 77 |
| PreS$_2$-TLM-CBD3$_{acetylated}$ | PLSSIFSRIGDPARSRLAELRGVPRGL | 78 |
| PreS$_2$-TLM-CBD3$_{\Box7-15}$ | PLSSIFSRIGDPARSRLA | 79 |
| HTLV-II REX-CBD3 | TRRQRTRRARRNRARSRLAELRGVPRGL | 80 |
| HTLV-II REX-CBD3$_{A6K}$ | TRRQRTRRARRNRARSRLKELRGVPRGL | 81 |
| HTLV-II REX-CBD3$_{R9L}$ | TRRQRTRRARRNRARSRLAELLGVPRGL | 82 |
| HTLV-II REX-CBD3$_{G14F}$ | TRRQRTRRARRNRARSRLAELRGVPRFL | 83 |
| HTLV-II REX-CBD3$_{amidated}$ | TRRQRTRRARRNRARSRLAELRGVPRGL | 84 |
| HTLV-II REX-CBD3$_{acetylated}$ | TRRQRTRRARRNRARSRLAELRGVPRGL | 85 |
| HTLV-II REX-CBD3$_{\Box7-15}$ | TRRQRTRRARRNRARSRLA | 86 |
| MAP-CBD3 (ST3-104) | KLALKLALKALKAALKLAARSRLAELRGVPRGL | 87 |
| MAP-CBD3$_{A6K}$ | KLALKLALKALKAALKLAARSRLKELRGVPRGL | 88 |
| MAP-CBD3$_{R9L}$ | KLALKLALKALKAALKLAARSRLAELLGVPRGL | 89 |
| MAP-CBD3$_{G14F}$ | KLALKLALKALKAALKLAARSRLAELRGVPRFL | 90 |
| MAP-CBD3$_{amidated}$ | KLALKLALKALKAALKLAARSRLAELRGVPRGL | 91 |
| MAP-CBD3$_{acetylated}$ | KLALKLALKALKAALKLAARSRLAELRGVPRGL | 92 |
| MAP-CBD3$_{\Box7-15}$ | KLALKLALKALKAALKLAARSRLA | 93 |
| TP-CBD3 | AGYLLGKINLKALAALAKKILARSRLAELRGVPRGL | 94 |
| TP-CBD3$_{A6K}$ | AGYLLGKINLKALAALAKKILARSRLAELLGVPRGL | 95 |
| TP-CBD3$_{R9L}$ | AGYLLGKINLKALAALAKKILARSRLAELLGVPRGL | 96 |
| TP-CBD3$_{G14F}$ | AGYLLGKINLKALAALAKKILARSRLAELRGVPRFL | 97 |
| TP-CBD3$_{amidated}$ | AGYLLGKINLKALAALAKKILARSRLAELRGVPRGL | 98 |
| TP-CBD3$_{acetylated}$ | AGYLLGKINLKALAALAKKILARSRLAELRGVPRGL | 99 |
| TP-CBD3$_{\Box7-15}$ | AGYLLGKINLKALAALAKKILARSRLA | 100 |
| PEP-CBD3 | KETWWETWWTEWSQPKKKRKVARSRLAELRGVPRGL | 101 |
| PEP-CBD3$_{A6K}$ | KETWWETWWTEWSQPKKKRKVARSRLEKLRGVPRGL | 102 |
| PEP-CBD3$_{R9L}$ | KETWWETWWTEWSQPKKKRKVARSRLAELLGVPRGL | 103 |
| PEP-CBD3$_{G14F}$ | KETWWETWWTEWSQPKKKRKVARSRLAELRGVPRFL | 104 |
| PEP-CBD3$_{amidated}$ | KETWWETWWTEWSQPKKKRKVARSRLAELRGVPRGL | 105 |
| PEP-CBD3$_{acetylated}$ | KETWWETWWTEWSQPKKKRKVARSRLAELRGVPRGL | 106 |
| PEP-CBD3$_{\Box7-15}$ | KETWWETWWTEWSQPKKKRKVARSRLA | 107 |
| PrP-CBD3 | MALNLGWLLALFVTMWTDVGLCKKRPKPARSRLAELRGVPRGL | 108 |
| PrP-CBD3$_{A6K}$ | MALNLGWLLALFVTMWTDVGLCKKRPKPARSRLKELRGVPRGL | 109 |
| PrP-CBD3$_{R9L}$ | MALNLGWLLALFVTMWTDVGLCKKRPKPARSRLAELLGVPRGL | 110 |

-continued

| Peptide Conjugate (T-A) | Sequence | SEQ ID NO: |
|---|---|---|
| PrP-CBD3$_{G14F}$ | MALNLGWLLALFVTMWTDVGLCKKRPKPARSRLAELRGVPRFL | 111 |
| PrP-CBD3$_{amidated}$ | MALNLGWLLALFVTMWTDVGLCKKRPKPARSRLAELRGVPRGL | 112 |
| PrP-CBD3$_{acetylated}$ | MALNLGWLLALFVTMWTDVGLCKKRPKPARSRLAELRGVPRGL | 113 |
| PrP-CBD3$_{\square 7-15}$ | MALNLGWLLALFVTMWTDVGLCKKRPKPARSRLA | 114 |

TATm is modified TAT peptide consisting of 13 amino acids and has a half-life of ~8.8 hrs. TATm is derived from the TAT protein, which is an 86-amino acid protein involved in the replication of human immunodeficiency virus type 1 (HIV-1). It has been reported that exogenous TAT protein is able to translocate through the plasma membrane and to reach the nucleus to transactivate the viral genome. A region of the TAT protein centered on a cluster of basic amino acids has been assigned to this translocation activity. Recent data have demonstrated that chemical coupling of a TAT-derived peptide (extending from residues 37 to 72) to several proteins allowed their functional internalization into several cell lines or tissues. (Vives et al., A Truncated HIV-1 TAT Protein Basic Domain Rapidly Translocates Through the Plasma Membrane and Accumulates in the Cell Nucleus. J. Biol. Chem. 1997, 272, 16010-16017).

PTD peptides are described in Derossi et al., The Third Helix of the Antennapedia Homeodomain Translocates Through Biological Membranes. J. Biol. Chem. 1994, 269, 10444-104450.

pVEC is an 18 amino acid peptide from vascular endothelial cadherin (Elmquist et al., VE-Cadherin-Derived Cell-Penetrating Peptide, pVEC, with Carrier Functions. Exp. Cell Res. 2001, 269, 237-244.)

R9 is oligoarginine (SEQ ID NO: 1). Homopolymers or peptides containing a high percentage of cationic amino acids have been shown to have the ability to cross the plasma membrane of cells, and consequently have been used to facilitate the uptake of a variety of biopolymers and small molecules. (Mitchell et al., Polyarginine Enters Cells More Efficiently Than Other Polycationic Homopolymers. J. Pept. Res. 2000, 56, 318-325).

PreS$_2$-TLM is derived from an amphipatic alpha-helix between amino acids 41 and 52 of PreS2 domain in the junction area of the PreS2- and S-domain of the hepatitis-B virus surface antigens; this domain demonstrates a cell permeability feature that is not restricted to hepatocytes (Oess & Hildt, Novel Cell Permeable Motif Derived from the PreS2-Domain of Hepatitis-B Virus Surface Antigens. Gene Ther. 2000, 7, 750-758.). The half-life is reportedly ~4.4 hrs (Sarko et al., 2010 Molecular Pharmaceutics 7(6): 2224-2231).

MAP is Model amphipathic peptide. MAP's uptake into mammalian cells involves non-endocytic mechanisms. MAP is a model peptide in serving as a vector for intracellular delivery of polar bioactive compounds. (Oehlke et al., Cellular Uptake of an Alpha-Helical Amphipathic Model Peptide with the Potential to Deliver Polar Compounds into the Cell Interior Non-Endocytically. Biochim. Biophys. Acta 1998, 1414, 127-139).

TP is transportan, a 21 amino acid peptide with a half-life of greater than 72 hrs with reduced undesirable cellular activity (Soomets et al., Deletion Analogues of Transportan. Biochim. Biophys. Acta 2000, 1467, 165-176).

EXAMPLE. Identification of CRMP2 binding peptides within CaV. A short peptide (CBD3) derived from CRMP2, a novel binding partner of CaV2.2 (10), disrupts the CaV2.2-CRMP2 interaction leading to a physiologically relevant decrease in Ca$^{2+}$ current and neurotransmitter release and, in turn, suppression of persistent inflammatory and neuropathic hypersensitivity (11). Molecular mapping revealed direct binding between CRMP2 and two intracellular regions on CaV2.2—the first intracellular loop (L1; amino acids 356 to 483) and the distal third of the carboxyl-terminus (Ct-dis; amino acids 2119 to 2336) (10). Short peptides from the L1 or Ct-dis regions of the channel were evaluated for the ability to disrupt the interaction and affect Ca$^{2+}$ signaling, transmitter release, and behavioral hypersensitivity. A peptide array was created to identify shorter regions within these large L1 and Ct-dis regions that coordinated binding to CRMP2, harboring 15-mer peptides, with an overlap of 10 amino acids, from the L1 and Ct-dis regions of CaV2.2. Because of significant (~60%) homology of this region to CaV2.1 (P/Q-type), CaV2.3 (R-type), CaV1.2 (L-type), the L1 regions of these channels were also tiled. Although multiple sequence alignment revealed lesser (<30%) homology between Ct-dis regions of these channels, these regions were also tiled for completion. These spots, along with spots harboring peptides against GST (negative control) were then probed in a far-Western manner with a CRMP2 antibody. Quantification of the intensity of the CRMP2 immunoreactivity on the spots identified several L1 and Ct-dis peptides from all four Ca$^{2+}$ channel isoforms was performed as a matrix representation of normalized fluorescent intensity of CRMP2 binding to immobilized 15-mer L1 peptides of N (CaV2.2)-type, P/Q (CaV2.1)-type, R(CaV2.3)-type and L (CaV1.2)-type calcium channels, and a matrix representation of normalized fluorescent intensity of CRMP2 binding to immobilized 15-mer L1 peptides of N (CaV2.2)-type, P/Q (CaV2.1)-type, R(CaV2.3)-type and L (CaV1.2)-type calcium channels. The matrix was generated with Matrix2png software (55). For L1 peptides, CRMP2 binding clustered around the 9$^{th}$ spot harboring a sequence that was relatively well conserved across the four Ca$^{2+}$ channel isoforms, as shown in the following table, where the sequence enclosed in parentheses corresponds to the L1 peptide.

| Channel | Peptide (a) | SEQ ID NO: |
|---|---|---|
| CaV2.2 | NG(YLEWIFKAEEVMLAE)ED | 115 |
| CaV2.1 | NG(YMEWISKAEEVILAE)DE | 116 |
| CaV2.3 | NG(YRAWIDKAEEVMLAE)EN | 117 |
| CaV1.2 | KG(YLDWITQAEDIDPEN)ED | 118 |
|  | *(*   **   **    ) |  |

(a) amino acids 386-404, where the numbering corresponds to CaV2.2. The 9$^{th}$ peptide from CaV2.2 corresponds to the sequence YLEWIFKAEEVMLAE (SEQ ID NO: 125), and the (*) indicate residues that are fully conserved between the channel subtypes.

In contrast, Ct-dis peptides bound CRMP2 at various spots spread throughout the sequence of the four Ca$^{2+}$ channel isoforms, as shown in the following table, where the sequence enclosed in parentheses corresponds to the Ct-dis peptide.

| Channel | Peptide (a) | SEQ ID NO: |
|---|---|---|
| Ct-Dis (CaV1.2 (L)) | AESSEKL(NSSFPSIHCSSWSEE)TTACSGG | 119 |
| Ct-Dis (CaV2.1 (P/Q)) | SITYKTA(NSSPV------HFAE)GQSGLPA | 120 |
| Ct-Dis (CaV2.3 (R)) | LVSYSPA(PRRP---------AA)RRMAGPP | 121 |
| Ct-Dis (CaV2.2 (N)) | LLSYSSL(MRHTGGISP--PPDG)SEGGSPL | 122 |

(a) amino acids 2007-2035, rat sequence, where the numbering corresponds to CaV1.2. However, despite little homology between the 24$^{th}$ Ct-dis peptide (amino acids 2014-2028 of L-type) to the other three Ca$^{2+}$ channel isoforms, the corresponding regions in the other three Ca$^{2+}$ channel isoforms around this peptide displayed relatively high binding to CRMP2. The 24$^{th}$ peptide from CaV1.2 that exhibited the highest binding to CRMP2 corresponds to the sequence NSSFPSIHCSSWSEE (SEQ ID NO: 127).

EXAMPLE. Synthesis and blotting of SPOTS membranes SPOTS blots (25) encompassing the first intracellular loops and distal third of the carboxyl termini of N-, P/Q-, R- and L-type calcium channels were synthesized, using standard 9-fluorenylmethoxycarbonyl (Fmoc) chemistry, in 30×20 spot arrays using a Multipep peptide synthesizer adapted for SPOTS synthesis (Intavis AG, Cologne, Germany). Membranes were blocked for at least 1 h in Tris-buffered saline containing 0.5% Tween 20 (TBST) with 5% skim milk powder before incubation for 1 hr with a purified rat brain synaptosome fraction at room temperature with gentle shaking. Following a series of brief washes in TBST, the blot was probed overnight with a polyclonal CRMP2 antibody at 4° C. The following day, blots were washed three times for 10 min each time in TBST, incubated in secondary antibody (horseradish peroxidase-conjugated goat anti-rabbit; 1:10,000) for 45 min at room temperature, washed for 30 min in TBST three more times for 10 min each time before visualizing SPOTS by exposing the membranes to enhanced chemiluminescence reagent.

EXAMPLE. Construction of glutathione S-transferase (GST) fusion proteins. Oligonucleotides for the distal third of the carboxyl terminus of CaV1.2 (nucleotides 5961-6695 of rat sequence, GenBank Accession #: NM_012517) were purchased from Sigma. This Ct-dis region was amplified from cDNA prepared from post-natal day 1 rat brain and cloned into the BamHI/MfeI-cut pGex-3x-Glu vector. Construction of the CaV2.2 Ct-dis-pGex-3x-Glu vector has been described previously (10).

EXAMPLE. Purification of CRMP2-His and CaV1.2-Ct-dis- and CaV2.2-Ct-dis-GST fusion proteins. GST fusion proteins were purified from BL21 (DE3) *Escherichia coli* bacterial lysates as described previously (10,11) while CRMP2-His protein was purified as before (26) with the following modifications. Expression of CRMP-2-His was induced with 1 mM isopropyl-β-d-thiogalactopyranoside (IPTG). For purification, following overnight growth at 16° C., transformed bacteria were pelleted at 5,000×g for 20 min at 4° C. and lysed in His lysis buffer (50 mM HEPES pH 7.4, 150 mM NaCl) using a M-110L Microfluidizer (Microfluidics Corp., Newton, Mass.). The lysate was then clarified by spinning at 30,000×g for 45 min at 4° C. before being filtered through a 0.45 µm syringe filter. The filtered supernatant was loaded onto a Talon™ metal affinity resin (Clontech, Mountain View, Calif.) column pre-equilibrated with His wash buffer (50 mM HEPES, pH 7.4, 150 mM NaCl, 10 mM imidazole). The column was washed with 2× column volumes of His wash buffer and His proteins eluted with His elution buffer (50 mM HEPES, pH 7.4, 150 mM NaCl, 100 mM imidazole). Elution fractions were separated by SDS-PAGE and fractions containing CRMP-2 were combined. The combined elution fractions were then dialyzed against protein storage buffer (10 mM HEPES, pH 7.4, 100 mM NaCl, and 20 mM CaCl$_2$). Purified protein concentration was determined from densitometric scans of protein bands resolved on a SDS-PAGE stained by colloidal Coomassie blue (Pierce) against a bovine serum albumin standard curve. Additionally, protein identity was verified by immunoblotting.

Method Examples

EXAMPLE. Statistical analyses. Differences between means were compared by either paired or unpaired two-tailed Student's t-tests. Transmitter release measurements, represented as percent total content of iCGRP, are expressed as the mean±standard error of the mean (SEM). All differences in iCGRP release and total content were compared with analyses of variance (ANOVAs) and Dunnett's post hoc analysis or Student's t-tests, as indicated. Behavioral threshold values were statistically analyzed for each foot separately and the significance of differences between the average of at least two pre-injection tests and the mean obtained for each post-injection test. In all tests, baseline data were obtained for the ddC-treated and sham-treated groups before drug or vehicle administration. Within each treatment group, post-administration means were compared with the baseline values by repeated measures analyses of variance (RMANOVA) followed by post hoc pairwise comparisons (Student-Newman-Keuls Method). A p value of <0.05 was used to indicate statistical significance between treatment and non-treatment groups.

EXAMPLE. Microscale thermophoresis (MST) binding analyses. MST, the directed movement of molecules in optically generated microscopic temperature gradients, permits an immobilization-free fluorescence methodology for the analysis of interaction of biomolecules (27,28). This thermophoretic movement is determined by the entropy of the hydration shell around molecules. The microscopic temperature gradient is generated by an infrared laser. In a typical MST-experiment the concentration of the labeled molecule is kept constant, while the concentration of the unlabeled interaction partner is varied. A constant concentration of dye NT647-labeled CRMP2 (labeled protein concentration of 20 μM) was incubated for 10 min at room temperature in the dark with different concentrations of L1 or Ct-dis peptides (up to 5000 nM) in 20 mM Tris, 150 mM NaCl, 0.01 mM EDTA with 0.01% Tween-20. Immediately afterwards, 3-5 μL of the samples were loaded into standard glass capillaries (Monolith NT Capillaries, NanoTemper) and the thermophoresis analysis was performed on a NanoTemper Monolith NT.115 instrument (40% LED; 40% IR-laser power). The MST curves were fitted with a Hill method using Origin8.5 software to obtain Kd values for binding between CRMP2 and peptides.

EXAMPLE. Catecholamine A differentiated (CAD) cell culture. CAD cells were cultured exactly as previously described (29,30).

EXAMPLE. Transfection of CAD cells. CAD cells were transfected using polyethylenimine (PEI) as previously described (31). Briefly, cells were transfected at ~60% confluency using a experimentally optimized ratio of DNA:PEI. DNA and PEI were mixed and allowed to incubate for 5 min at room temperature prior to addition to cells.

EXAMPLE. Generation of CAD cell and DRG ganglia lysates, immunoprecipitation, and immunoblotting. CAD cells were lysed two days following transfection using a modified RIPA buffer (50 mM Tris-HCl pH 8.0, 150 mM NaCl, 1% NP-40, 0.5% Na-deoxycholate, and 1 mM EDTA supplemented with fresh protease inhibitors) with gentle agitation at 4° C. for 10 min. Samples were then clarified by centrifugation at 10,000×g for 20 min. The supernatant was saved and used for subsequent immunoprecipitations and immunoblotting as previously described (10,11,32).

To assess if CaV peptides can interfere with the association between CRMP2 and calcium channels, lysate from ~40-60 ganglia from adult rats, devoid of nerve roots, were lysed in modified RIPA buffer and subjected to immunoprecipitation with anti-CaV2.2 antibody in the absence or presence of control, TAT-L1 and TAT-Ct-dis peptides (10 μM each added 30 min prior to addition of antibody). Immunoblotting was performed as described (11,33).

EXAMPLE. Primary dorsal root ganglion (DRG) neuronal cultures. Isolation of sensory neurons from 1 to 2 month old wildtype C57BL/6J and Nf1$^{+/-}$ C57BL/6J littermates (34) was performed exactly as described previously (11,35,36) while DRGs from adult rats were prepared as per Brittain and colleagues (11). All animals were housed, bred, and had free access to food and water in the Indiana University Laboratory Animal Research Center and used in procedures approved by the Animal Use and Care Committee of the Indiana University School of Medicine. All animals were genotyped prior to use in experiments.

EXAMPLE. Calcium imaging. DRG neurons were loaded at 37° C. with 2.6 μM Fura-2FF-AM (Kd=25 μM, λex 340, 380 nm/λemi 512 nm) to follow changes in $[Ca^{2+}]_c$ in a standard bath solution containing 139 mM NaCl, 3 mM KCl, 0.8 mM MgCl$_2$, 1.8 mM CaCl$_2$, 10 mM NaHEPES, pH 7.4, 5 mM glucose. Fluorescence imaging was performed with an inverted microscope, Nikon Eclipse TE2000-U, using objective Nikon Super Fluor 20×0.75 NA and a Photometrics cooled CCD camera CoolSNAPHQ (Roper Scientific, Tucson, Ariz.) controlled by MetaFluor 6.3 software (Molecular Devices, Downingtown, Pa.). The excitation light was delivered by a Lambda-LS system (Sutter Instruments, Novato, Calif.). The excitation filters (340±5 and 380±7) were controlled by a Lambda 10-2 optical filter change (Sutter Instruments, Novato, Calif.). The excitation filters (340±5 and 380±7) were controlled by a Lambda 10-2 optical filter change (Sutter Instruments, Novato, Calif.). Fluorescence was recorded through a 505 nm dichroic minor at 535±25 nm. To minimize photobleaching and phototoxicity, the images were taken every 15 seconds during the time-course of the experiment using the minimal exposure time that provided acceptable image quality. The changes in $[Ca^{2+}]_c$ were monitored by following a ratio of F340/F380, calculated after subtracting the background from both channels.

EXAMPLE. Stimulated-release of iCGRP. Measurement of stimulus-evoked release and content of immunoreactive CGRP (iCGRP) from isolated sensory neurons was accomplished as previously published (11,33,35). After 5-7 days in culture, media was removed and the basal or resting release of iCGRP was measured from cells incubated for 10 minutes in HEPES buffer consisting of (in mM): 25 HEPES, 135 NaCl, 3.5 KCl, 2.5 CaCl$_2$, 1 MgCl$_2$, 3.3 dextrose, and 0.1% (w/v) bovine serum albumin, pH 7.4, and maintained at 37° C. The cells were incubated in HEPES buffer containing stimulus (50 mM KCl) for 10 minutes, and then incubated again with HEPES buffer with 3.5 mM KCl to re-establish resting release levels. The amount of iCGRP released in each incubation was measured by a radioimmunoas say (RIA). The minimum amount of iCGRP detected by the RIA is 5 fmol with a 95% confidence interval (37). After the release protocol, the remaining peptide content in each well was determined by exposing the cells to 2 N acetic acid for 10 minutes. Aliquots of acid solution were diluted in HEPES and iCGRP levels were determined by RIA. The release of iCGRP during the 10 min incubation period is expressed as percent of the total content. A minimum of three different preparations were used for each condition.

EXAMPLE. Biophysical characterization of CRMP2 binding to L1 and Ct-dis peptides. It has been reported that in in vitro binding assays, full-length Ct-dis binds CRMP2 with a higher affinity (~75-fold) than full-length L1 (10). The short 15-mer peptides of these regions, [388-402] L1 and [2014-2028] Ct-dis are evaluated for binding to CRMP2 using microscale thermophoresis (MST) (27,39). Using an infrared-laser precise microscopic temperature gradients are generated within thin glass capillaries filled with a fluorescently-labeled protein sample in a buffer and the atomistic movement of molecules along these temperature gradients is monitored in the presence of increasing concentrations of an unlabeled binding partner. CRMP2 diffuses away from the heated spot, causing a local depletion and drop in fluorescence. Peptide binding changes the thermophoretic properties of CRMP2, resulting in a decreased thermodiffusion. Changes in fluorescence intensity in the capillaries are used to calculate binding affinity between biomolecules. MST measurements were made on NT647-labeled CRMP2 in the presence of increasing amounts (10-13 different peptide concentrations ranging from 0 to 5 μM) of L1 or Ct-dis peptides. As the concentration of the peptides increased, they bound to CRMP2 thermodiffusing out of the heated infrared spot resulting in a decrease in the MST signal and providing a readout of the binding between the CRMP2 and the peptides. The binding curves are fitted with the Hill method to obtain Kd values for binding between CRMP2 and peptides. L1 peptide bound to CRMP2 with a Kd of 3.12±0.31 μM while the Ct-dis peptide bound to CRMP2 with a Kd of 0.64±0.10 μM. Additional experiments using isothermal titration calorimetry revealed a similar 5 to 7 fold difference in binding affinities between L1 and Ct-dis binding to CRMP2. These results demonstrate that the peptides described herein, including the 15 mer peptides and peptide conjugates derived from CaV, bind CRMP2.

EXAMPLE. L1 and Ct-dis peptides block interaction between CaV2.2 and CRMP2. Immunoprecipitation from rat dorsal root ganglia with CaV2.2 antibody in the presence of L1 or Ct-dis (10 μM) peptides reduced the amount of CRMP2 that could be captured from rat DRGs, but not the prototypical CaV2.2 binding protein syntaxin (40), that was recovered. Peptides (10 μM each) were added for 30 min prior to addition of the peptides. Similar results were obtained in experiments with rat brain lysates. These results demonstrate that the peptides described herein, including the L1 and Ct-dis peptides, are sufficient to uncouple the interaction between CaV2.2 and CRMP2.

Although the Ct-dis peptide was able to bind and inhibit the interaction between CaV2.2 and CRMP2, it is derived from the L-type (i.e. CaV1.2), supporting that this $Ca^{2+}$ channel isoform can bind to CRMP2. A neuronal CAD cell line that endogenously expresses L-type CaV 1.2 channels was transfected with Flag-tagged CRMP2 and tested if the proteins could form a complex. All Flag-tagged constructs expressed detectable levels of the fusion protein. CAD cells were transfected with cDNAs encoding Nipsnap-1-, Nipsnap-2-, or CRMP2-3xFlag. A novel role of Nipsnap2 in transcriptional regulation via L-type $Ca^{2+}$ channels has been recently reported (31). Precipitation of CRMP2 (with a Flag antibody) from lysates of these cells co-precipitated CaV1.2. CaV1.2 was detected in CAD lysates expressing CRMP2 but not Nipsnap1 or 2. As negative controls, lysates immunoprecipitated with Flag antibody from cells expressing Flag-tagged Nipsnap1/2 proteins—which regulate but not associate with CaV1.2 (31)—did not capture CaV1.2.

To examine if the Ct-dis region of CaV 1.2 interacts with CRMP2, bacterially expressed GST fusion CaV1.2 Ct-dis were cloned and purified and incubated with rat brain lysates. The in vitro complexes were recovered with glutathione-Sepharose beads, washed extensively and immunoblotted with CRMP2. CaV1.2 Ct-dis bound to CRMP2. CaV2.2 Ct-dis also bound to CRMP2 as reported previously (10). Collectively, these biochemical results demonstrate that CRMP2 exists in a biochemical complex with CaV1.2, and that the peptides and peptide conjugates described herein, including Ct-dis peptide, are capable of binding CRMP2 and inhibiting the interaction between CaV2.2 and CRMP2.

EXAMPLE. L1 and Ct-dis peptides affect $K^+$-stimulated $Ca^{2+}$ influx. Uncoupling the CaV2.2-CRMP2 interaction with a peptide derived from CRMP2 results in reduction of depolarization-induced $Ca^{2+}$-influx in sensory neurons (11). As described herein, interfering with the CaV2.2-CRMP2 complex with a peptide derived from the opposite interface can achieve the same result. Calcium imaging experiments performed with Fura-2-FF-AM on adult rat DRG neurons showed that stimulation with high $K^+$ (46.5 mM) produced a transient increase of $[Ca^{2+}]_c$ in response to plasma membrane depolarization. Differential interference contrast (DIC) and pseudocolored fluorescent images of a field of DRG neurons visualized for Fura-2, before and after stimulation with KCl (Hi $K^+$). $Ca^{2+}$ imaging was performed on adult rat DRG neurons using the ratiometric $Ca^{2+}$-sensitive dye Fura-2. Following a 1 min baseline measurement, neurons were stimulated with 46.5 mM KCl for 30-40 sec to induce $Ca^{2+}$ influx. DRGs incubated for 20 min with L1 or Ct-dis peptides showed a concentration-dependent decrease in $K^+$-stimulated $[Ca^{2+}]_c$ influx (FIG. 1). At 30 μM, peptide-mediated inhibition of $[Ca^{2+}]_c$ influx was much more pronounced for Ct-dis than L1 (FIG. 1). These results show that the peptides and peptide conjugates described herein, including L1 and Ct-dis peptides, affect $Ca^{2+}$ influx.

Figure 2:
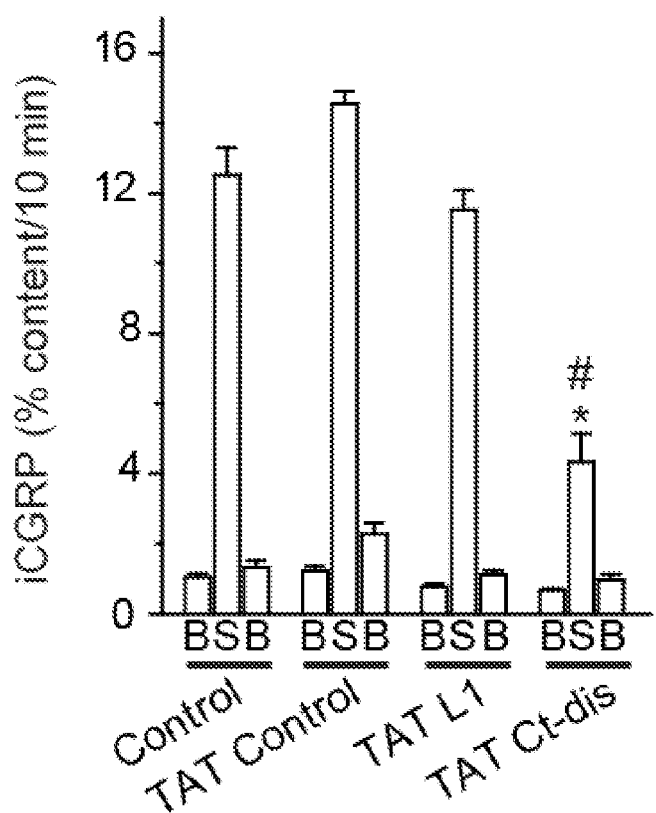
FIG. 2 shows a bar graph of immunoreactive calcitonin gene-related peptide (iCGRP) release expressed as mean percent total iCGRP content of cells in each well±s.e.m. (n=12-16 wells per condition). Asterisk (*) indicate statistically significant differences in iCGRP release between TAT-Ct-dis and all other groups using an ANOVA with Dunnett's post-hoc test ($p<0.05$). In all cases, release stimulated by high extracellular $K^+$ was significantly higher than basal release.

EXAMPLE. Ct-dis, but not L1, peptide affects $K^+$-evoked transmitter release from isolated sensory neurons. CRMP2 expression levels affect release of the neuropeptide transmitter calcitonin gene related-peptide (CGRP) from sensory neurons (33). Adult mouse DRG neurons were maintained in culture for 5-7 days prior to the release experiments. Disrupting the CaV2.2-CRMP2 interaction with the CBD3 peptide suppressed evoked CGRP release in sensory neurons in culture as well as spinal cord slices (11), highlighting the importance of this interaction for transmitter release. The peptides derived from the reciprocal interface, i.e. the channel itself, also affect release. The KCl-stimulated release of CGRP was measured from sensory neurons exposed to TAT-control, TAT-L1 or TAT-Ct-dis peptides, at 10 μM (a concentration at which $Ca^{2+}$ influx was largely unaffected by both peptides), included in the 10 minutes prior to and throughout the high $K^+$ exposures (total peptide exposure of 30 min). Neuropeptide release was measured from cells treated with successive incubations of normal HEPES buffer containing 3.5 mM KCl (basal, B), HEPES buffer containing 50 mM KCl (S), and HEPES buffer containing 3.5 mM KCl, again. The peptides were included in the 10 minutes prior to and throughout the high $K^+$ exposures (total peptide exposure of 30 min). The levels of basal or resting release of immunoreactive CGRP (iCGRP) were not significantly different between the groups: 1.53±0.10% total peptide content/10 min (n=12 wells) in untreated control neurons, 1.58±0.17% total peptide content/10 min (n=12 wells) in TAT-control peptide-treated neurons, 1.04±0.09 total peptide content/10 min (n=12 wells) in TAT-L1 peptide-treated neurons, and 0.92±0.09% total peptide content/10 min (n=16 wells) in TAT-control peptide-treated neurons (FIG. 2). A 10 min stimulation with 50 mM KCl evoked a robust increase (~12 to 14-fold over basal) in iCGRP release in untreated, TAT-control and TAT-L1-treated neurons. In contrast, neurons exposed to TAT-Ct-dis peptide had significantly (~70%) less iCGRP release compared to TAT-control (one-way ANOVA, FIG. 2), demonstrating that CaV2.2 peptides affect $K^+$-stimulated transmitter release in DRG neurons. Without being bound by theory, it is believed herein that the decrease in KCl-stimulated iCGRP release observed in TAT-Ct-dis-treated neurons was not caused by a decrease in the total cellular content of iCGRP as there was no significant difference in neuropeptide content in any of the four conditions.

Figure 3:
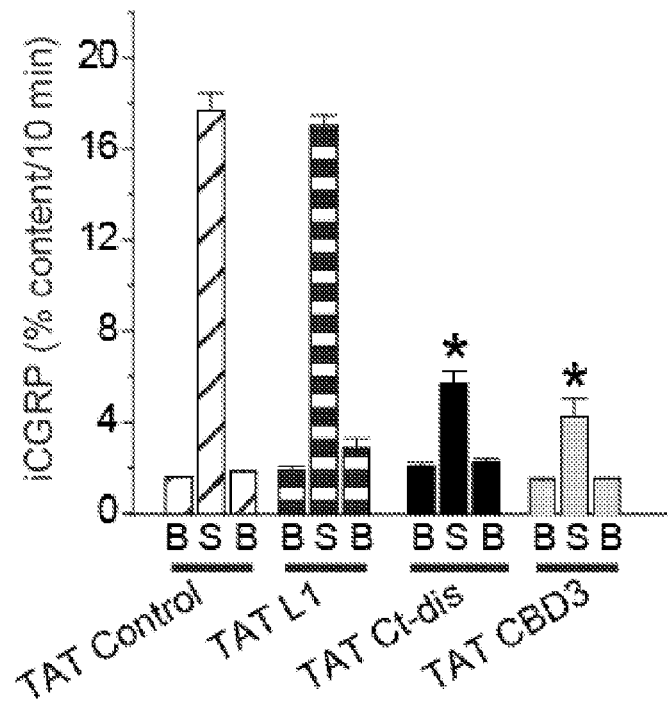
FIG. 3 shows a bar graph of iCGRP release expressed as mean percent total iCGRP content of cells in each well±s.e.m. (n=12 wells/condition). Asterisk (*) indicate statistically significant differences in iCGRP release between TAT-Ct-dis or TAT-CBD3 and TAT-control using an ANOVA with Dunnett's post-hoc test ($p<0.05$).

EXAMPLE. The CaV peptides also affect the release of CGRP in sensory neurons isolated from $Nf^{+/-}$ mice, which reportedly have increased N-type calcium currents as well as enhanced transmitter release of glutamate (36) and CGRP (35). Neurofibromin, the protein whose deficiency leads to neurofibromatosis type 1, is a binding partner of CRMP2 (41) and it is not known if disrupting the CRMP2-CaV2.2 interaction could affect CGRP release in these neurons. KCl-stimulated release of CGRP was measured from sensory neurons exposed to 10 μM TAT-conjugated peptides as indicated for wild type neurons. Adult $Nf1^{+/-}$ mice DRG neurons were maintained in culture for 5-7 days prior to the release experiments. Neuropeptide release was measured from cells as described in the previous example. The levels of basal or resting release of iCGRP were not significantly different between the groups (FIG. 3). A 10 min stimulation with 50 mM KCl evoked a robust increase (~8 to 10-fold over basal) in iCGRP release in untreated and TAT-control treated neurons. In contrast, neurons exposed to TAT-Ct-dis peptide had significantly (~70%) less iCGRP release compared to TAT-control (one-way ANOVA, FIG. 3). CaV2.2 peptides affect $K^+$-stimulated transmitter release in DRG neurons from Nf1$^{+/-}$ mice. The CRMP2 peptide CBD3 also inhibited CGRP release by ~78% compared to TAT-control neurons (FIG. 3). Without being bound by theory, it is believed herein that the decrease in KCl-stimulated iCGRP release observed in TAT-Ct-dis- or TAT-CBD3-treated neurons was not caused by a decrease in the total cellular content of iCGRP as there was no significant difference in neuropeptide content in any of the four conditions. The KCl-stimulated increase in iCGRP occurred largely via N-type Ca$^{2+}$ channels as 500 nM ω-CTX inhibited iCGRP release by ~50% compared to untreated neurons. Collectively, these results indicate that disrupting CRMP2-CaV2.2 interactions impact release of the neuropeptide transmitter iCGRP in sensory neurons.

Figure 4:
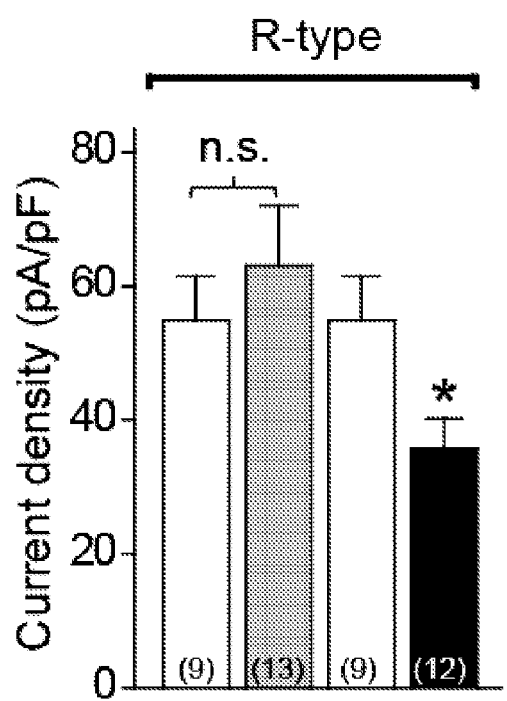
FIG. 4 shows bar graphs illustrating the average R-type calcium current densities (pA/pF)±SEM values for neurons treated with vehicle (white), 10 µM ST1-104 (grey) or 10 µM ST1-106 (black) bath-applied for at least 10 min. The number of cells is indicated in parentheses. The asterisk denote statistical significance ($p<0.05$; one-way analysis of variance with Dunnett's post-hoc test) compared to untreated control cells.

EXAMPLE. Compounds described herein significantly reduce R-type (CaV2.3) Ca$^{2+}$ currents in sensory neurons as shown in FIG. 4 for ST1-106. Currents were evoked by 200 ms steps in 5 mV increments from −60 mV (to minimize contribution of T-type currents) to +50 mV, from a holding potential of −90 mV. To isolate R-type Ca$^{2+}$ currents, the extracellular bath solution contained 5 μM Nifedipine, 200 nM ω-Agatoxin IVA and 500 nM ω-Conotoxin GVIA to block L-, P/Q-, and N-type calcium currents, respectively. ST1-106 showed a significant decrease over control; ST1-104 did not show a significant decrease over control at the treatment concentration/

Figure 5:
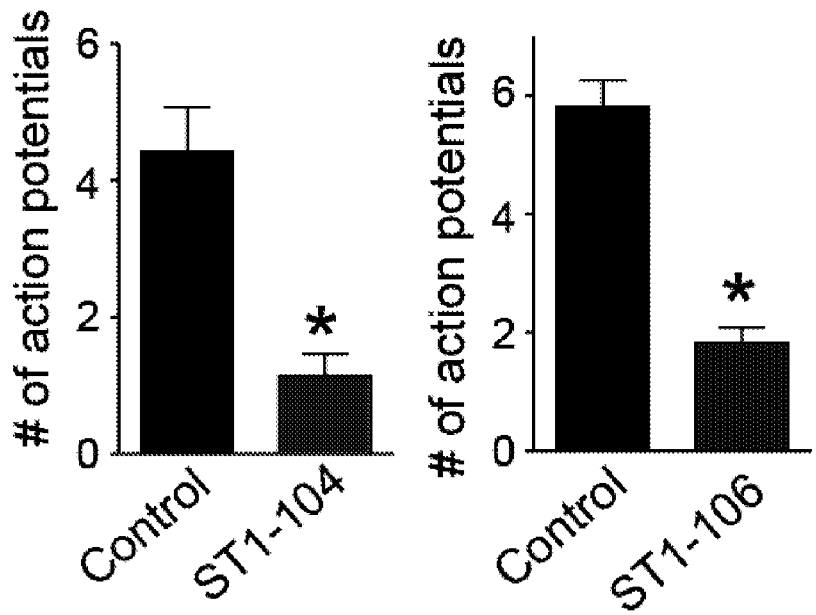
FIG. 5 shows that ST1-104 (C) and ST1-106 (E) caused a significant reduction in DRG action potential firing (*, $p<0.05$ versus control, Student's t-test; n=8 each).

EXAMPLE. Compounds described herein significantly reduce excitability of d4T-treated sensory neurons by decreasing AP number, as shown in the following FIG. 5 for ST1-104 and ST1-106. Current clamp recordings were performed on small-to-medium (>30 μm->40 μm) diameter lumbar 4-5 DRG neurons from d4T-treated rats. Firing of 4-6 action potentials (APs) was elicited by a 1 second depolarizing current injection (ranging from 0.1 to 0.4 nA depending on the cell) every 30 seconds. The recordings demonstrated that application of 10 μM ST1-104 or 10 μM ST1-106 reduces the number of elicited action potentials.

EXAMPLE. ddC model of peripheral neuropathy. Hyperalgesia and allodynia were established by a single injection (50 mg/kg) of the antiretroviral drug 2',3'-dideoxycytidine (ddC, Sigma) given intraperitoneal (i.p) in 150-200 g Sprague Dawley rats. A single administration of ddC produced a significant bilateral decrease in paw withdrawal threshold to von Frey hair stimulation from post-injection day 3 through 21, the last day of testing. The von Frey test was performed on six positions spaced across the glabrous side of the hind paw; two distinct locations for the distribution of each nerve branch (saphenous, tibial and sural) exactly as described previously to determine paw withdrawal threshold (PWT) to tactile stimuli (11,38). Baseline threshold measurements were performed for 3 successive days prior to i.p. injection of ddC. Stimuli were applied randomly to left and right hind paws to determine the stimulus intensity threshold stiffness required to elicit a paw withdrawal response. The incidence of foot withdrawal was expressed as a percentage of six applications of each filament as a function of force. A Hill equation was fitted to the function (Origin version 6.0, Microcal Software) relating the percentage of indentations eliciting a withdrawal to the force of indentation. From this equation, the threshold force was obtained and defined as the force corresponding to a 50% withdrawal rate. A threshold that exhibits at least a −20 mN difference from the baseline threshold of testing in a given animal is representative of neuropathic pain (11,38).

Figure 6:
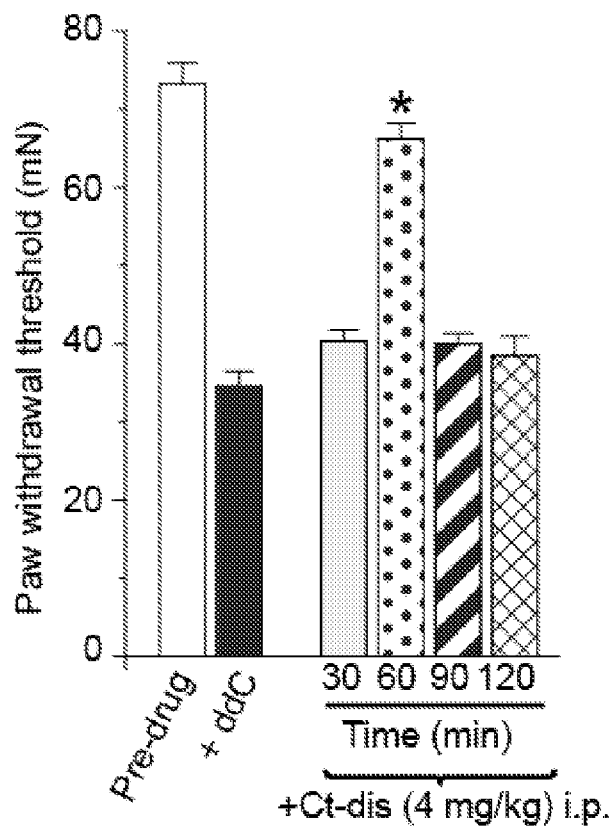
FIG. 6 shows paw-withdrawal thresholds (PWT in millinewtons, MN) measured in ddC-treated rodents exhibiting mechanical hypersensitivity before and after intraperitoneal administration of the indicated peptides.

EXAMPLE. Ct-dis peptide attenuates AIDS therapy-induced painful peripheral neuropathy. The effects of the Ct-dis was examined on chronic nociceptive behavior in an animal model of AIDS therapy-induced painful neuropathy (11,13,38). Nucleoside reverse transcriptase inhibitors (NRTIs), commonly used for AIDS treatment, produce side-effects including painful neuropathies. The ability of peptides to reverse tactile hypersensitivity was evaluated in rats seven days after a single injection of ddC. TAT-Ct-dis peptide caused a time-dependent increase in PWT when administered intraperitoneally (i.p.) (FIG. 6). Almost complete reversal of tactile hypersensitivity was observed at the ~4 mg/kg dose of TAT-Ct-dis 1 h after i.p. injection. Two hours after injection, the peptide-induced reversal of hypersensitivity had diminished to pre-peptide levels, which may be accounted for by degradation and biodistribution of the peptide, indicating that the compounds described herein decrease ddC-induced mechanical hypersensitivity. After the induction of neuropathic pain behavior using ddC, TAT Ct-dis (4 mg/kg body weight) was administered and bilateral pain behavior was assessed using the Von-Frey filament test. Behavior was tested at 30, 60, 90 and 120 minutes. Following a single injection of ddC, the bilateral paw withdrawal threshold required to elicit a response was significantly reduced (n=6; black bar). Following administration of TAT-Ct-dis, bilateral paw withdrawal thresholds increased to pre-ddC levels (ANOVA with Dunnett's post hoc test, *p<0.05). A scramble control peptide (10 mg/kg) or saline controls did not elicit any change in PWT at any time tested following i.p. injection of ddC-injected rats.

EXAMPLE. Neuropathic Animal Model, Rodent Model of DN. Diabetes affects 25.8 million people in the US. Diabetic neuropathy (DN) pain is present in 3 of 10 individuals with diabetes and exerts a substantial impact on the quality of life. Despite this significant impact and prevalence, current therapies for DN are only partially effective in diabetic patients. The mouse and rat models of type 2 diabetes mellitus are used to evaluate the efficacy of the peptides and peptide conjugates described herein. Type 2 diabetes is a metabolic disorder that is characterized by high blood glucose in the context of insulin resistance and insulin deficiency. Leptin-deficient ob/ob mice (Pelleymounter et al., 1995) are widely accepted as an animal model of type 2 diabetes that develops DN (Drel et al., 2006;Vareniuk et al., 2007). A mutation in the leptin receptor produces mice that are hyperphagic and obese, develop severe type 2 diabetes with marked hyperglycemia. These mice develop diabetes by 4 weeks and DN by 8 weeks of age, with evidence of DN that includes prolonged thermal latencies, mechanical allodynia, slowed nerve conduction velocities, and loss of intraepidermal nerve fiber density. Heterozygous (db/+) mice do not develop diabetes and are used as nondiabetic controls (Sima and Robertson, 1978). It is appreciated herein that there may be some advantage to the use of rats over mice for behavioral pain studies. Accordingly, the inbred Bio-Breeding Zucker diabetic rat (BBZDR)/Wor rat strain (Sima et al., 2000) is also used to evaluate the efficacy of the peptides and peptide conjugates described herein. The strain was created to introgress the defective leptin receptor gene (Leprfa) from insulin resistant Zucker fatty rats into the inbred BBDR/Wor strain background (Obrosova, 2009;Sima et al., 2000). Similar to diabetes type 2 patients the BBZDR/ Wor rat develops complications with hyperglycemia including pronounced DN by 10 weeks (Tirabassi et al., 2004). These diabetic rats are also commonly used models for DN (see Wright Support letter). The compounds described herein, including ST1-104, are efficacious in reversing mechanical hyperalgesia in a type I diabetes model in mice Briefly, diabetes is induced by administration of streptozocin (STZ) (Sigma, St. Louis, Mo.) intraperitoneally (200 mg/kg), dissolved in 0.4 ml sodium citrate buffer, pH 4.5 into eight-week-old male C57BL/6 mice (Charles River, Wilmington, Mass.). Control mice are injected only with 0.4 ml sodium citrate buffer (Wan, Z. Dohle, Friemann green 1993 Diabetes 42:420). Mice are monitored closely for symptoms of hyperglycemia, which include polydipsia, polyuria, and weight loss. Mice are weighed at weekly intervals and blood glucose levels are measured at sacrifice using the Glucose Diagnostic Kit 510-DA (Sigma). In one variation using STZ-injected mice, only mice with reduced body weight and blood glucose levels greater than 16.7 mmol/L are included in the diabetic group (Akkina S K, Patterson C L, Wright D E, 2001; Experimental Neurology 167:173).

Figure 8:
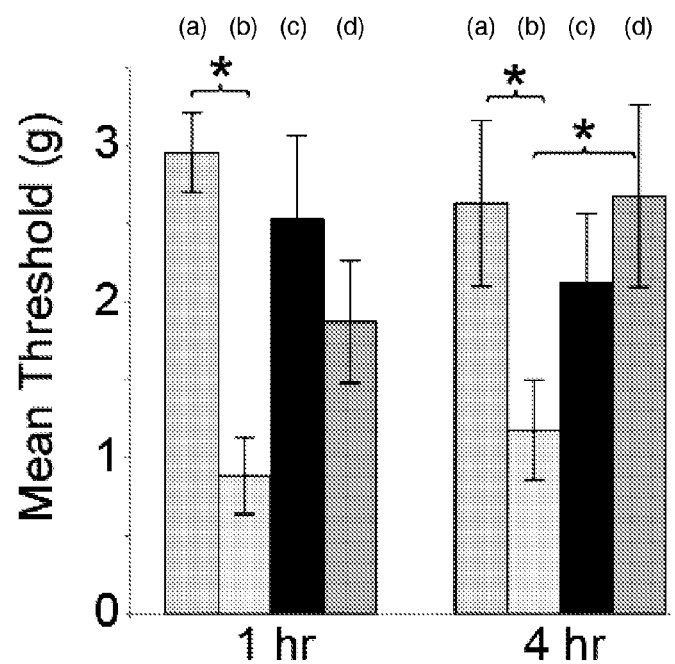
FIG. 8 shows that the mean paw withdrawal threshold was reversed by ST1-104 (d) in diabetic (DB) mice (d) compared to non-diabetic (N-DB) mice (c) when each is compared to vehicle control ((b) DB-vehicle and (a) N-DB vehicle, respectively) (*, $p<0.01$, RMANOVA with Newman-Keuls post hoc test; n=5).

EXAMPLE. Compounds described herein, such as TAT-CBD3 (ST1-104), attenuate mechanical hyperalgesia in a diabetic (DB) model. A type 1 diabetes was induced in A/J mice with 2 injections of streptozocin to kill insulin producing beta cells. Four weeks later, the mice are given an i.p. injection of test compound, such as ST1-104 (10 mg/kg), or vehicle and assessed 1 and 4 hr later. The mean paw withdrawal threshold are reversed by ST1-104 in DB compared to non-diabetic (N-DB) mice as shown in FIG. 8 (*, $p<0.01$, RMANOVA with Newman-Keuls post hoc test; n=5).

Figure 7:
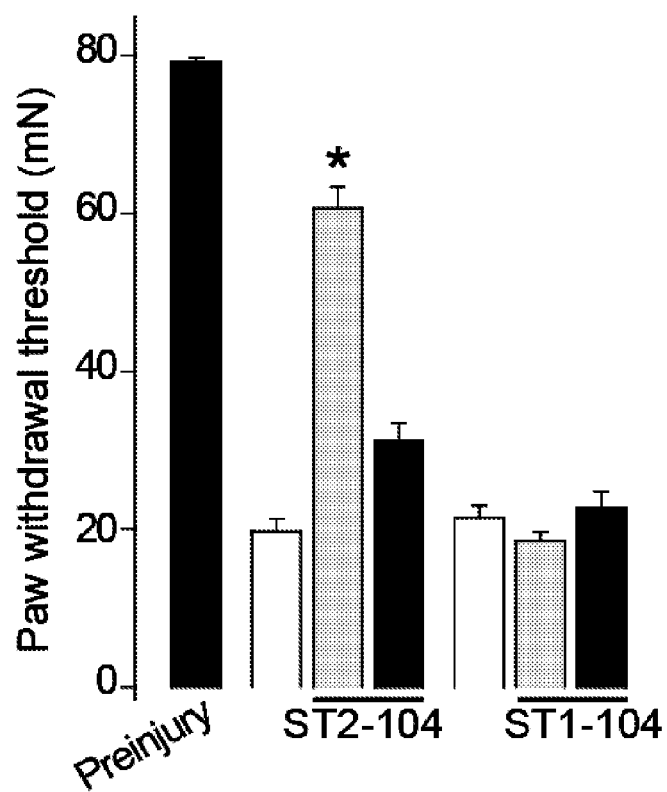
FIG. 7 shows that paw-withdrawal thresholds in tibial nerve injury rats exhibiting mechanical hypersensitivity are reversed by an i.p. injection of ST2-104 but not ST1-104 when administered at 10 mg/kg and evaluated at 1 h (grey bars) versus 4 h (black bars), compared to vehicle treated controls (white bars) (*, $p<0.01$, RMANOVA with Newman-Keuls post hoc test; n=6).

EXAMPLE. Compounds described herein reverse neuropathic hypersensitivity induced by a nerve injury, as shown in FIG. 7 for ST2-104. ST2-104 is tagged with a cell penetrating sequence comprising a stretch of 9 arginine (R9) residues. ST2-104-reverses nerve-injury induced nociception at the tested concentration, but ST1-104 does not. It is appreciated herein that the R9 carrier peptide may be superior to the TAT peptide and allow for the administration of lower doses of drug.

Figure 12:
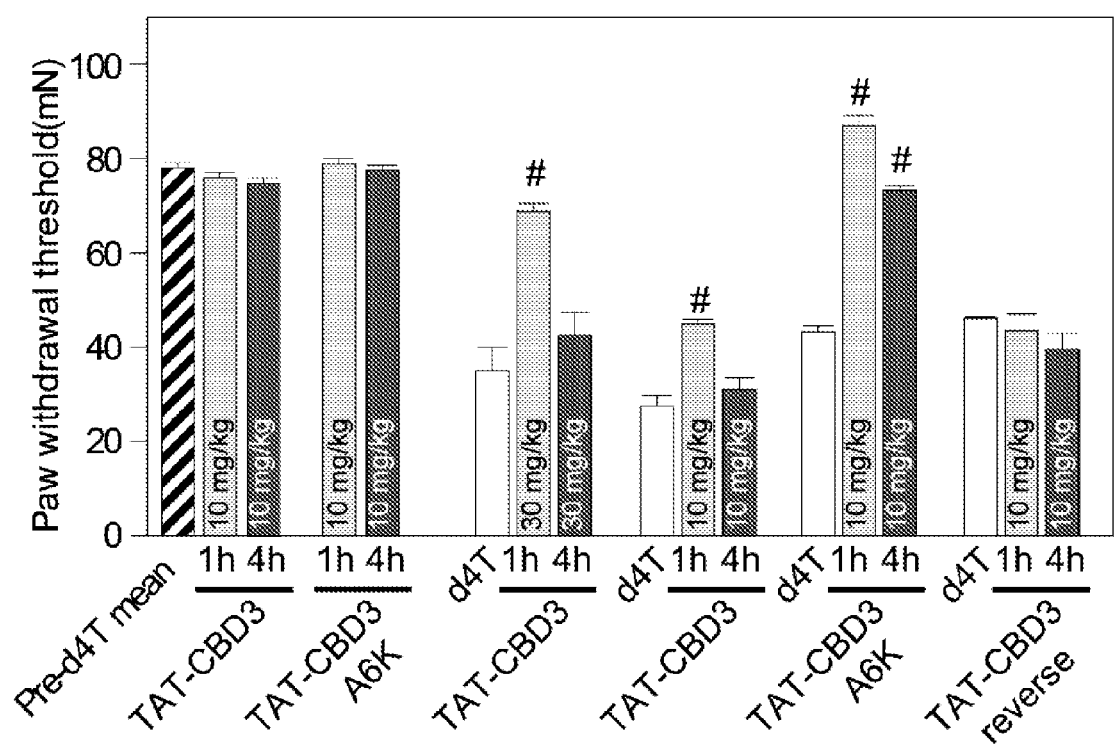
FIG. 12 shows the paw-withdrawal thresholds (PWT in millinewtons, mN) for healthy animals and d4T-treated animals (a mechanical hypersensitivity animal model) treated with vehicle (white bars) compared to TAT-CBD3 (ST1-104), TAT-CBD3$_{A6K}$ (ST1-105), and TAT-CDB3-reverse peptide at various doses.

EXAMPLE. d4T-induced mechanical hypersensitivity. Compounds described herein, such as TAT-CBD3 and TAT-CBD3A6K peptides, significantly increase pain tolerance in d4T-induced mechanical hypersensitivity animal models. Paw-withdrawal thresholds were measured in d4T-treated rodents exhibiting mechanical hypersensitivity before and after administration of TAT-CBD3, TAT-CBD3A6K mutant peptide, and TAT-CBD3 reverse peptide. Nociceptive thresholds are significantly reduced in d4T-treated rodents in untreated or vehicle treated controls (FIG. 12, white bars). As shown in FIG. 12, a single intraperitoneal (i.p.) administration of TAT-CBD3 at 30 mg/kg body weight, or 10 mg/kg body weight, attenuates d4T-induced mechanical hypersensitivity for at least 1 hour (#, $p<0.01$, RMANOVA with Newman-Keul post hoc test; n=6). Also shown in FIG. 12, administration of a 10 mg/kg i.p. dose of TAT-CBD3A6K significantly attenuated d4T-induced peripheral hypersensitivity for at least 4 hours (#, $p<0.01$, RMANOVA with Newman-Keul post hoc test; n=6). Also shown in FIG. 12, administration of a 10 mg/kg i.p. dose of TAT-CBD3 reverse peptide did not alter d4T-mechanical hypersensitivity (n=3). Neither TAT-CBD3 nor TAT-CBD3A6K administered at 10 mg showed an effect on healthy animals (pre-d4T).

EXAMPLE. Hyperalgesia diabete (DB) model. Compounds described herein, such as TAT-CBD3 (ST1-104) attenuate mechanical hyperalgesia in a diabetic (DB) model. A type 1 diabetes was induced in A/J mice with 2 injections of streptozocin to kill insulin producing beta cells. Four weeks later, the mice were given an i.p. injection of ST1-104 (10 mg/kg) or vehicle and assessed 1 and 4 hr later. As shown in FIG. 8, the mean paw withdrawal threshold was reversed by ST1-104 in DB (d) compared to non-diabetic (N-DB) (c) mice (*, $p<0.01$, RMANOVA with Newman-Keuls post hoc test; n=5).

EXAMPLE. Neuropathic Animal Model, Rodent Model of Nucleoside Reverse Transcriptase Inhibitor-induced DSP. Human immunodeficiency virus (HIV)-related DSP is the most common HW-associated sensory neuropathy. Rodent models of HIV-DSP may be used to evaluate the efficacy of the peptides and peptide conjugates described herein. However, it is appreciated that such models may be inadequate given the nature of the disease. Alternatively, HW-DSP may be evaluated following the administration of the antiretroviral drug class of nucleoside reverse transcriptase inhibitors (NRTIs) which HIV-infected patients take to treat their disease. NRTIs produce side-effects including painful neuropathies and many conventional agents utilized as pharmacologic therapy for neuropathic pain are not effective for providing satisfactory analgesia in painful HIV-related distal sensory polyneuropathy. To elucidate the underlying mechanisms involved in NRTI-induced DSP, a model of nucleoside analog reverse transcriptase inhibitor-induced painful peripheral neuropathy in the rat is developed as described herein, using 2',3'-dideoxycytidine (ddC) and 2',3'-didehydro-3'-deoxythymidine (d4T) (Bhangoo et al., 2007; Ripsch et al., 2012). ddC (trade name Hivid® (Zalcitibine)) was withdrawn by the FDA in 2007 and discontinued by the manufacturer due to NRTI-induced DSP. d4t (Zerit® (Stavudine)) remains FDA-approved despite inducing DSP. In 2009, the World Health Organization recommended that countries phase out the use of d4t because of the long-term, irreversible DSP. However, d4t is still widely used in first-line therapy in many countries due to its low cost and widespread availability.

Briefly, the drugs, 2',3'-dideoxycytidine (ddC) (Sigma-Aldrich, St Louis, Mo., USA) are employed. The drug is freshly prepared in saline on the day of the experiment. ddC- and vehicle-treated groups are given a one-time intraperitoneal (i.p.) injection of ddC (25 mg/kg) or saline (vehicle), respectively (Bhangoo et al., 2007; BBI).

Figure 9:
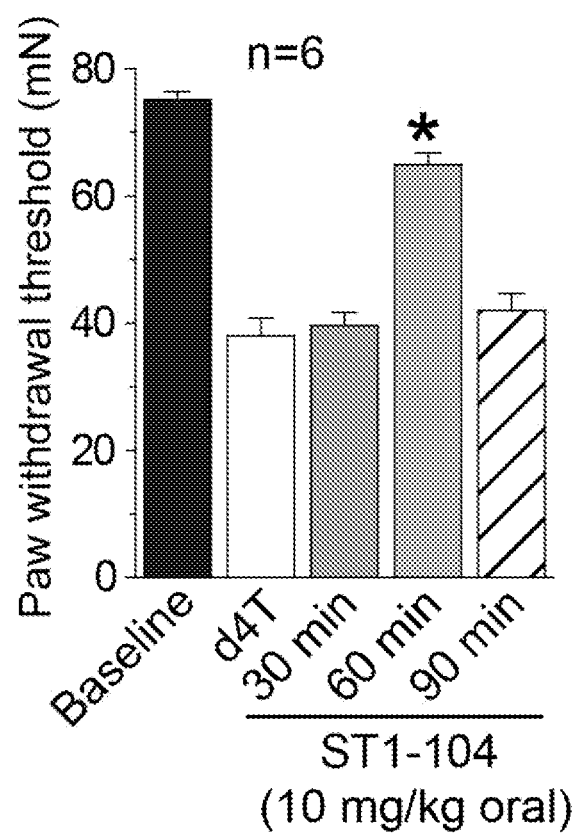
FIG. 9 shows that paw-withdrawal thresholds in d4T-treated rats exhibiting mechanical hypersensitivity are reversed by a 10 mg/kg oral dosage of ST1-104 (in nutella) (*, $p<0.01$, RMANOVA with Newman-Keuls post hoc test; n=6).

EXAMPLE. Compounds described herein, such as ST1-104, administered orally reverse neuropathic hypersensitivity induced by anti-retroviral drugs, as shown in FIG. 9.

Figure 10:
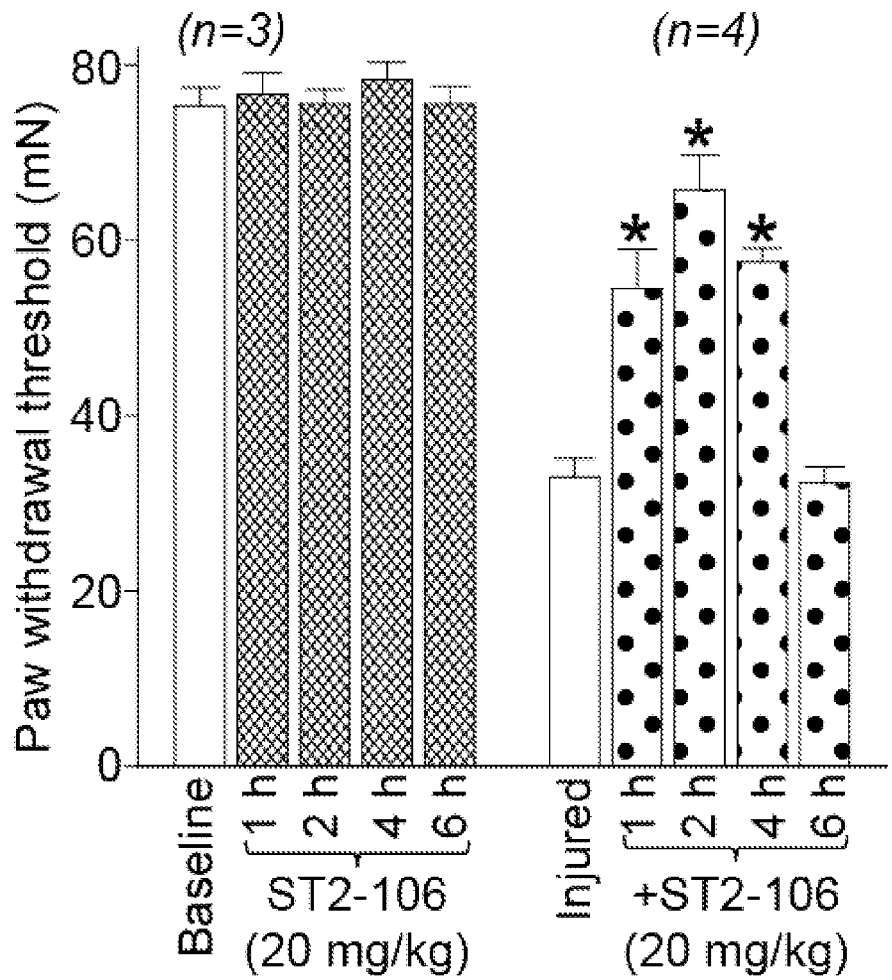
FIG. 10 shows paw-withdrawal thresholds (PWT in millinewtons; mN) measured in naïve (left) and TNI (right) rodents before and after intraperitoneal administration of ST2-106. PWT was unaffected by systemic administration of the peptide in naïve animals. PWT in TNI rodents was significantly reduced when compared to pre-TNI thresholds (n=6; white bar). Following intraperitoneal administration of ST2-106 (20 mg/kg body weight), PWT returned to pre-TNI levels for at least 4 hours (ANOVA with Dunnett's post hoc test, *$p<0.05$).

EXAMPLE. Antinociceptive efficacy following acute and continuous systemic infusion. Test animals with tibial nerve injury (TNI)-induced neuropathic pain behavior (over 6 months) were administered to a single intraperitoneal injection or continual constant-rate infusion of polyarginine-conjugated CBD3A6K (ST2-106). Female Sprague-Dawley rats with TNI were administered a single injection of saline or 20 mg/kg of ST2-106. As shown in FIG. 10, a single intraperitoneal injection of 20 mg/kg of ST2-106 produced antinociception for 4 hours in TNI rats without any effects on thermal or tactile nociceptive behavioral changes. Compounds described herein, such as polyarginine-CBD3A6K (ST2-106) peptide, reverse tibial nerve injury (TNI) induced mechanical hypersensitivity following a single administration.

Female Sprague-Dawley rats with TNI were infused with saline or ST2-106 over a 24 to 72 hour period using subcutaneously implanted Alzet® osmotic minipumps. In contrast to the single injection treatment, injured animals receiving infusion of ST2-106 exhibited a pronounced reduction in tactile hypersensitivity starting at 8 hours following pump implantation and lasting approximately 20 to 62 hours. Rats were used at 28 days after tibial nerve injury.

Paw-withdrawal thresholds (PWT in millinewtons, mN) were measured in naïve rats and rats subjected to spared nerve injury (i.e. tibial nerve ligation, TNI). PWT in rodents subjected to injury is significantly reduced when compared to baseline(BL)/naïve thresholds. Continuous infusion of saline administered via a subcutaneous Alzet osmotic pump did not alter hypersensitivity of rats with injury (inj./pre-pump) (red squares). ST2-106 administration (0.17 mg/h) for 24 hours via the Alzet subcutaneous pump elicited a ~20 h reduction in tactile hypersensitivity starting at 8 hours following pump implantation and lasting for 4 h after cessation of infusion (*, p<0.01, RMANOVA with Newman-Keuls post hoc test; n=4). No changes in ambulation/locomotion or feeding were observed in rats treated for 24 h with ST2-106.

Figure 11:
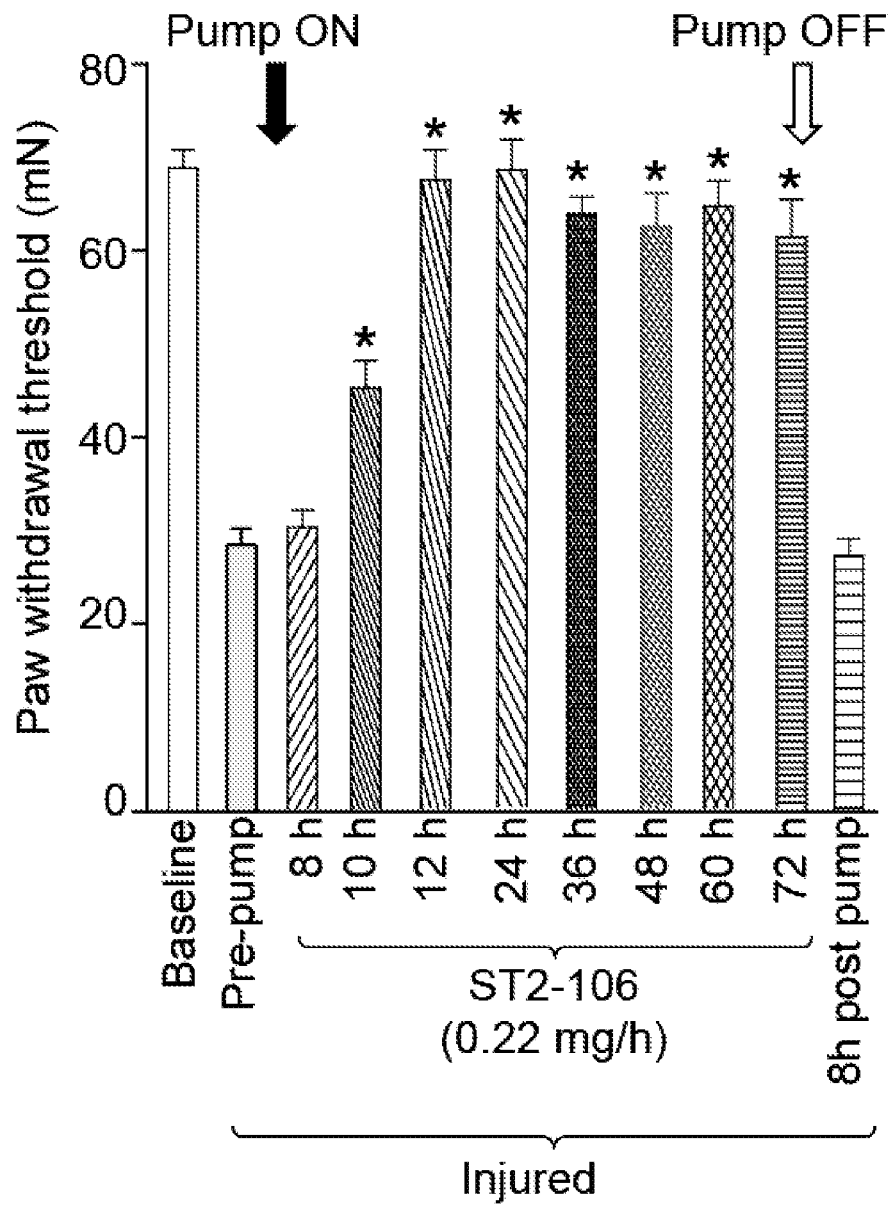
FIG. 11 shows the paw-withdrawal thresholds (PWT in millinewtons, mN) following continuous infusion of ST2-106 (0.17 mg/h) for 72 hours via the Alzet subcutaneous pump elicited a ~62 h reduction in tactile hypersensitivity starting at 10 hours following pump implantation and lasting till 72 h (*, $p<0.01$, RMANOVA with Newman-Keuls post hoc test; n=4).

Paw-withdrawal thresholds (PWT in millinewtons, mN) were also measured in naïve rats and rats subjected to TNI when treated with compounds described herein or vehicle for extended periods. Continuous infusion of saline administered via a subcutaneous Alzet osmotic pump did not alter hypersensitivity of rats with injury (inj./pre-pump). ST2-106 administration (0.17 mg/h) for 72 hours via the Alzet subcutaneous pump elicited a ~62 h reduction in tactile hypersensitivity starting at 10 hours following pump implantation and lasting till 72 h, as shown in FIG. 11 (*, p<0.01, RMANOVA with Newman-Keuls post hoc test; n=4). No changes in ambulation/locomotion or feeding were observed in rats treated for 24 h with ST2-106.

It is believed herein that mechanistically, ST2-106 concentration-dependently inhibited the CaV2.2-CRMP2 interaction and surface expression of CaV2.2 in rat sensory neurons. Functionally, ST2-106 concentration-dependently inhibited depolarization-evoked $Ca^{2+}$ influx in sensory neurons and suppressed excitability of small to medium diameter sensory neurons likely via inhibition of T-type and R-type $Ca^{2+}$ channels. These results validate the therapeutic significance of targeting the CaV-CRMP2 axis for relief of chronic neuropathic pain.

EXAMPLE. Continuous systemic administration of ST2-106 did not show any negative effects on motor activity, memory, or learning or cause evidence of anxiety or depression. Continuous infusion of ST2-106 (R9-CBD3-A6K) does not affect anxiety, general activity, or spatial memory of rodents. ST2-106 administration (0.167 mg/h) for 20 hours via the Alzet subcutaneous pump did not affect distance traveled, duration of immobility (time stationary) or freezing, or time spent in the inner regions of the testing box compared to vehicle control in a conventional open-field test. Time spent with a familiar object (FO) or a novel object (NO) was not different between treatment conditions in the novel object recognition test of spatial memory. Anxiety and depression/despair like behaviors were also not different between treatment conditions. The naïve rats were tested at ~20 h after pump implantation, a time at which peak reversal in hypersensitivity was observed in injured rats. Heat maps are a compilation of the activity of 8 rats per group. n.s., p>0.05, RMANOVA with Newman-Keuls post hoc test; n=8. Unpublished data.

ST2-106 administration (0.167 mg/h) for 72 hours via the Alzet subcutaneous pump did not affect distance traveled, duration of immobility (time stationary) or freezing, or time spent in the inner regions of the testing box compared to vehicle control in a conventional open-field test (p>0.05, RMANOVA with Newman-Keuls post hoc test; n=8). The naïve rats were tested at ~20 h after pump implantation, a time at which peak reversal in hypersensitivity was observed in injured rats.

EXAMPLE. Neuropathic Animal Model, Rodent Model of Spinal stenosis. Trauma or degenerative disc disorders leading to foraminal stenosis often contributes to chronic lower back pain or sciatica in humans. The pain is felt in the lower back, buttock, or various parts of the leg and foot. In addition to pain, which is sometimes severe, there may be numbness, muscular weakness, pins and needles or tingling (parethesia) and difficulty in moving or controlling the leg. Chronic compression of the DRG (CCD model) has been used to mimic chronic lower back pain or sciatic compression in rodents and is produced in adult rats by implanting two stainless steel rods unilaterally into the L4 and L5 intervertebral foramen (Song et al., 1999). Paw withdrawal is used as evidence of a hypersensitive response to mechanical and thermal stimulation of the plantar surface. Ectopic spontaneous discharges can be recorded from neurons with intact conducting nerve fibers within the chronically compressed ganglia (White et al., 2005). Interestingly, behavioral hyperalgesia after CCD treatment recovers quickly after the rod withdrawal (Song et al., 2003).

The animal model is prepared as follows. After anesthesia with pentobarbital sodium (40 mg/kg, i.p.), the paraspinal muscles are separated from the mammillary and transverse processes to expose the intervertebral foramina at lumbar DRG (L)4 and L5. A sharp stainless steel needle, 0.4 mm in diameter with a right angle to limit penetration, is inserted ~4 mm into the foramen at L4 and again at L5 in a rostral direction (≈30-40° angle) to the dorsal middle line and −10° to −15° below the vertebral horizontal line (Hu S J and Xin J L, 1998 *Pain*). After ~1 s, the needle is withdrawn, and a stainless steel rod, L-shaped, 4 mm in length and 0.63 mm in diameter, is implanted into each foramen. Each rod is oriented in a manner described for the needle. After the rod is in place, the muscle and skin layers are sutured. An antibiotic, Baytril (enrofloxacin, 2.5 mg/kg i.m., Bayer HealthCare, Shawnee Mission, Kans.) is administered immediately after surgery. Sham-operated control rats undergo the same surgical procedure as described, except that each rod will be withdrawn ~1 s after insertion (White, PNAS, 2005). For additional details, see Song et al., J Neurophysiology (1999)).

The following publications, and each of the additional publications cited herein are incorporated herein by reference:

1. Zamponi, G. W., Lewis, R. J., Todorovic, S. M., Arneric, S. P., and Snutch, T. P. (2009) *Brain Res. Rev.* 60, 84-89
2. Snutch, T. P. (2005) *NeuroRx.* 2, 662-670
3. Malmberg, A. B. and Yaksh, T. L. (1994) *J. Neurosci.* 14, 4882-4890
4. Bowersox, S. S., Gadbois, T., Singh, T., Pettus, M., Wang, Y. X., and Luther, R. R. (1996) *J. Pharmacol. Exp. Ther.* 279, 1243-1249
5. White, D. M. and Cousins, M. J. (1998) *Brain Res.* 801, 50-58
6. Souza, A. H., Ferreira, J., Cordeiro, M. N., Vieira, L. B., De Castro, C. J., Trevisan, G., Reis, H., Souza, I. A., Richardson, M., Prado, M. A., Prado, V. F., and Gomez, M. V. (2008) *Pain.* 140, 115-126
7. McGivern, J. G. (2007) *Neuropsychiatr. Dis. Treat.* 3, 69-85
8. Schmidtko, A., Lotsch, J., Freynhagen, R., and Geisslinger, G. (2010) *Lancet.* 375, 1569-1577
9. Bowersox, S. S., Singh, T., Nadasdi, L., Zukowska-Grojec, Z., Valentino, K., and Hoffman, B. B. (1992) *J Cardiovasc. Pharmacol.* 20, 756-764

10. Brittain, J. M., Piekarz, A. D., Wang, Y., Kondo, T., Cummins, T. R., and Khanna, R. (2009) *J. Biol. Chem.* 284, 31375-31390

11. Brittain, J. M., Duarte, D. B., Wilson, S. M., Zhu, W., Ballard, C., Johnson, P. L., Liu, N., Xiong, W., Ripsch, M. S., Wang, Y., Fehrenbacher, J. C., Fitz, S. D., Khanna, M., Park, C. K., Schmutzler, B. S., Cheon, B. M., Due, M. R., Brustovetsky, T., Ashpole, N. M., Hudmon, A., Meroueh, S. O., Hingtgen, C. M., Brustovetsky, N., Ji, R. R., Hurley, J. H., Jin, X., Shekhar, A., Xu, X. M., Oxford, G. S., Vasko, M. R., White, F. A., and Khanna, R. (2011) *Nat. Med.* 17, 822-829

12. Wilson, S. M., Brittain, J. M., Piekarz, A. D., Ballard, C. J., Ripsch, M. S., Cummins, T. R., Hurley, J. H., Khanna, M., Hammes, N. M., Samuels, B. C., White, F. A., and Khanna, R. (2011) *Channels (Austin.).* 5, 449-456

13. Ripsch, M. S., Ballard, C. J., Khanna, M., Hurley, J. H., White, F. A., and Khanna, R. (2012) *Translational Neuroscience* 3, 1-8

14. Bucci, G., Mochida, S., and Stephens, G. J. (2011) *J Physiol.* 589, 3085-3101

15. Mochida, S., Sheng, Z. H., Baker, C., Kobayashi, H., and Catterall, W. A. (1996) *Neuron.* 17, 781-788

16. Pragnell, M., De, W. M., Mori, Y., Tanabe, T., Snutch, T. P., and Campbell, K. P. (1994) *Nature.* 368, 67-70

17. DeWaard M., Liu, H., Walker, D., Scott, V. E., Gurnett, C. A., and Campbell, K. P. (1997) *Nature.* 385, 446-450

18. Li, B., Zhong, H., Scheuer, T., and Catterall, W. A. (2004) *Mol. Pharmacol.* 66, 761-769

19. Lee, A., Wong, S. T., Gallagher, D., Li, B., Storm, D. R., Scheuer, T., and Catterall, W. A. (1999) *Nature.* 399, 155-159

20. Peterson, B. Z., DeMaria, C. D., Adelman, J. P., and Yue, D. T. (1999) *Neuron.* 22, 549-558

21. Zuhlke, R. D., Pitt, G. S., Deisseroth, K., Tsien, R. W., and Reuter, H. (1999) *Nature.* 399, 159-162

22. Qin, N., Olcese, R., Bransby, M., Lin, T., and Birnbaumer, L. (1999) *Proc. Natl. Acad. Sci. U.S.A.* 96, 2435-2438

23. Van, P. F., Clark, K. A., Chatelain, F. C., and Minor, D. L., Jr. (2004) *Nature.* 429, 671-675

24. Tedford, H. W., Kisilevsky, A. E., Vieira, L. B., Varela, D., Chen, L., and Zamponi, G. W. (2010) *Mol. Brain.* 3:6., 6

25. Frank, R. (2002) *J Immunol. Methods.* 267, 13-26

26. Chan, A. W., Khanna, R., Li, Q., and Stanley, E. F. (2007) *Channels (Austin.).* 1, 11-20

27. Wienken, C. J., Baaske, P., Rothbauer, U., Braun, D., and Duhr, S. (2010) *Nat. Commun.* doi: 10.1038/ncomms1093., 100

28. van den Bogaart, G., Meyenberg, K., Diederichsen, U., and Jahn, R. (2012) *J Biol. Chem.*

29. Wang, Y. and Khanna, R. (2011) Voltage-gated calcium channels are not affected by the novel anti-epileptic drug lacosamide. *Transl. Neurosci.*

30. Wang, Y., Brittain, J. M., Jarecki, B. W., Park, K. D., Wilson, S. M., Wang, B., Hale, R., Meroueh, S. O., Cummins, T. R., and Khanna, R. (2010) *J. Biol. Chem.* 285, 25296-25307

31. Brittain, J., Wilson S. M, Wang, Y., and Khanna, R. (2012) *Channels* 6,

32. Brittain, J. M., Chen, L., Wilson, S. M., Brustovetsky, T., Gao, X., Ashpole, N. M., Molosh, A. I., You, H., Hudmon, A., Shekhar, A., White, F. A., Zamponi, G. W., Brustovetsky, N., Chen, J., and Khanna, R. (2011) *J. Biol. Chem.* 286, 37778-37792

33. Chi, X. X., Schmutzler, B. S., Brittain, J. M., Hingtgen, C. M., Nicol, G. D., and Khanna, R. (2009) *J. Cell Sci.* 23, 4351-4362

34. Jacks, T., Shih, T. S., Schmitt, E. M., Bronson, R. T., Bernards, A., and Weinberg, R. A. (1994) *Nat. Genet.* 7, 353-361

35. Hingtgen, C. M., Roy, S. L., and Clapp, D. W. (2006) *Neuroscience.* 137, 637-645

36. Wang, Y., Brittain, J. M., Wilson, S. M., Hingtgen, C. M., and Khanna, R. (2010) *Translational Neuroscience* 1, 106-114

37. Chen, J. J., Barber, L. A., Dymshitz, J., and Vasko, M. R. (1996) *Peptides.* 17, 31-37

38. Joseph, E. K., Chen, X., Khasar, S. G., and Levine, J. D. (2004) *Pain.* 107, 147-158

39. Zillner, K., Jerabek-Willemsen, M., Duhr, S., Braun, D., Langst, G., and Baaske, P. (2012) *Methods Mol. Biol.* 815:241-52., 241-252

40. Sheng, Z. H., Rettig, J., Takahashi, M., and Catterall, W. A. (1994) *Neuron.* 13, 1303-1313

41. Patrakitkomjorn, S., Kobayashi, D., Morikawa, T., Wilson, M. M., Tsubota, N., Irie, A., Ozawa, T., Aoki, M., Arimura, N., Kaibuchi, K., Saya, H., and Araki, N. (2008) *J. Biol. Chem.* 283, 9399-9413

42. Van, P. F. and Minor, D. L., Jr. (2006) *Biochem. Soc. Trans.* 34, 887-893

43. Qin, N., Platano, D., Olcese, R., Stefani, E., and Birnbaumer, L. (1997) *Proc. Natl. Acad. Sci. U.S.A.* 94, 8866-8871

44. Bell, T. J., Thaler, C., Castiglioni, A. J., Helton, T. D., and Lipscombe, D. (2004) *Neuron.* 41, 127-138

45. Altier, C., Dale, C. S., Kisilevsky, A. E., Chapman, K., Castiglioni, A. J., Matthews, E. A., Evans, R. M., Dickenson, A. H., Lipscombe, D., Vergnolle, N., and Zamponi, G. W. (2007) *J. Neurosci.* 27, 6363-6373

46. Winquist, R. J., Pan, J. Q., and Gribkoff, V. K. (2005) *Biochem. Pharmacol.* 70, 489-499

47. Cizkova, D., Marsala, J., Lukacova, N., Marsala, M., Jergova, S., Orendacova, J., and Yaksh, T. L. (2002) *Exp. Brain Res.* 147, 456-463

48. Saegusa, H., Kurihara, T., Zong, S., Kazuno, A., Matsuda, Y., Nonaka, T., Han, W., Toriyama, H., and Tanabe, T. (2001) *EMBO J.* 20, 2349-2356

49. Vanegas, H. and Schaible, H. (2000) *Pain.* 85, 9-18

50. Neugebauer, V., Vanegas, H., Nebe, J., Rumenapp, P., and Schaible, H. G. (1996) *J. Neurophysiol.* 76, 3740-3749

51. Sluka, K. A. (1997) *Pain.* 71, 157-164

52. Neugebauer, V., Rumenapp, P., and Schaible, H. G. (1996) *Neuroscience.* 71, 1095-1109

53. Fossat, P., Dobremez, E., Bouali-Benazzouz, R., Favereaux, A., Bertrand, S. S., Kilk, K., Leger, C., Cazalets, J. R., Langel, U., Landry, M., and Nagy, F. (2010) *J Neurosci.* % 20;30, 1073-1085

54. Favereaux, A., Thoumine, O., Bouali-Benazzouz, R., Rogues, V., Papon, M. A., Salam, S. A., Drutel, G., Leger, C., Calas, A., Nagy, F., and Landry, M. (2011) *EMBO J.* 30, 3830-3841

55. Pavlidis, P. and Noble, W. S. (2003) *Bioinformatics.* 19, 295-296

What is claimed is:

1. A peptide conjugate of the formula

T-A or a pharmaceutically acceptable salt thereof, wherein T is a carrier protein or peptide selected from the group consisting of TAT and R9, and A is peptide inhibitor selected from the group consisting of CBD3 (SEQ ID NO: 5), CBD3(A6K) (SEQ ID NO: 6) and CBD3(R9L) (SEQ ID NO: 7), wherein the peptide conjugate is capable of inhibiting a protein-protein-interaction between CRMP-2 and a calcium channel.

2. The conjugate of claim 1 wherein the calcium channel is CaV2.2.

3. The conjugate of claim 1 wherein T is TAT.

4. The conjugate of claim 1 wherein T is R9 (SEQ ID NO: 1).

5. The conjugate of claim 1 wherein A is CBD3 (SEQ ID NO: 5).

6. The conjugate of claim 1 wherein A is CBD3(A6K) (SEQ ID NO: 6).

7. The conjugate of claim 1 wherein A is CBD3(R9L) (SEQ ID NO: 7).

8. The peptide conjugate of claim 1 selected from the group consisting of TAT-CBD3, TAT-CBD3$_{A6K}$, TAT-CBD3$_{R9L}$, R9-CBD3, and R9-CBD3$_{R9L}$.

9. A pharmaceutical composition comprising a peptide conjugate of claim 1, and one or more carriers, diluents, or excipients, or a combination thereof.

10. A method for treating pain in a host animal, the method comprising the step of administering to the host animal a therapeutically effective amount of a peptide conjugate of claim 1, or a pharmaceutical composition thereof.

11. The method of claim 10 wherein the host animal is a human.

12. The method of claim 10 wherein the pain is pain associated with trauma.

13. The method of claim 10 wherein the pain is neuropathic pain.

14. The method of claim 10 wherein the pain is comorbid with diabetes.

15. The method of claim 10 wherein the pain is diabetic neuropathy.

16. The method of claim 10 wherein the pain is pain associated with therapy.

17. The method of claim 10 wherein the pain is pain associated with HIV treatment.

* * * * *

SEQUENCE LISTING

<160> NUMBER OF SEQ ID NOS: 154

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Arg Arg Arg Arg Arg Arg Arg
1               5

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Gly Arg Lys Lys Arg Arg Gln Arg Arg Arg Trp Glu Ala Lys Glu
1               5                   10                  15

Met Leu Tyr Phe Glu Ala Leu Val Ile Glu
            20                  25

<210> SEQ ID NO 3
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Gly Arg Lys Lys Arg Arg Gln Arg Arg Arg Tyr Leu Glu Trp Ile
1               5                   10                  15

Phe Lys Ala Glu Glu Val Met Leu Ala Glu
            20                  25

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Gly Arg Lys Lys Arg Arg Gln Arg Arg Arg Asn Ser Ser Phe Pro
1               5                   10                  15

Ser Ile His Cys Ser Ser Ser Trp Ser Glu Glu
            20                  25

<210> SEQ ID NO 5
<211> LENGTH: 15
<212> TYPE: PRT
<213> ORGANISM: Homo sapiens

<400> SEQUENCE: 5

Ala Arg Ser Arg Leu Ala Glu Leu Arg Gly Val Pro Arg Gly Leu
1               5                   10                  15

```
-continued

<210> SEQ ID NO 6
<211> LENGTH: 15
<212> TYPE: PRT
<213> ORGANISM: Homo sapiens

<400> SEQUENCE: 6

Ala Arg Ser Arg Leu Lys Glu Leu Arg Gly Val Pro Arg Gly Leu
1               5                   10                  15

<210> SEQ ID NO 7
<211> LENGTH: 13
<212> TYPE: PRT
<213> ORGANISM: Homo sapiens

<400> SEQUENCE: 7

Ala Arg Ser Arg Leu Ala Glu Leu Leu Pro Arg Gly Leu
1               5                   10

<210> SEQ ID NO 8
<211> LENGTH: 15
<212> TYPE: PRT
<213> ORGANISM: Homo sapiens

<400> SEQUENCE: 8

Ala Arg Ser Arg Leu Lys Glu Leu Leu Gly Val Pro Arg Gly Leu
1               5                   10                  15

<210> SEQ ID NO 9
<211> LENGTH: 15
<212> TYPE: PRT
<213> ORGANISM: Homo sapiens

<400> SEQUENCE: 9

Ala Arg Ser Arg Leu Ala Glu Leu Lys Gly Val Pro Arg Gly Leu
1               5                   10                  15

<210> SEQ ID NO 10
<211> LENGTH: 15
<212> TYPE: PRT
<213> ORGANISM: Homo sapiens

<400> SEQUENCE: 10

Ala Arg Ser Arg Leu Lys Glu Leu Lys Gly Val Pro Arg Gly Leu
1               5                   10                  15

<210> SEQ ID NO 11
<211> LENGTH: 15
<212> TYPE: PRT
<213> ORGANISM: Homo sapiens

<400> SEQUENCE: 11

Ala Arg Ser Arg Leu Ala Glu Leu Arg Gly Val Pro Arg Phe Leu
1               5                   10                  15

<210> SEQ ID NO 12
<211> LENGTH: 15
<212> TYPE: PRT
<213> ORGANISM: Homo sapiens

<400> SEQUENCE: 12

Ala Arg Ser Arg Leu Lys Glu Leu Arg Gly Val Pro Arg Phe Leu
1               5                   10                  15

<210> SEQ ID NO 13
<211> LENGTH: 15
```

```
<212> TYPE: PRT
<213> ORGANISM: Homo sapiens
<220> FEATURE:
<223> OTHER INFORMATION: C-term amidated

<400> SEQUENCE: 13

Ala Arg Ser Arg Leu Ala Glu Leu Arg Gly Val Pro Arg Gly Leu
1               5                   10                  15

<210> SEQ ID NO 14
<211> LENGTH: 6
<212> TYPE: PRT
<213> ORGANISM: Homo sapiens

<400> SEQUENCE: 14

Ala Arg Ser Arg Leu Ala
1               5

<210> SEQ ID NO 15
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Gly Arg Lys Lys Arg Arg Gln Arg Arg Ala Arg Ser Arg Leu
1               5                   10                  15

Ala Glu Leu Arg Gly Val Pro Arg Gly Leu
            20                  25

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Gly Arg Lys Lys Arg Arg Gln Arg Arg Ala Arg Ser Arg Leu
1               5                   10                  15

Lys Glu Leu Arg Gly Val Pro Arg Gly Leu
            20                  25

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Gly Arg Lys Lys Arg Arg Gln Arg Arg Ala Arg Ser Arg Leu
1               5                   10                  15

Ala Glu Leu Leu Gly Val Pro Arg Gly Leu
            20                  25

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 18

Tyr Gly Arg Lys Lys Arg Arg Gln Arg Arg Ala Arg Ser Arg Leu
1               5                   10                  15

Ala Glu Leu Lys Gly Val Pro Arg Gly Leu
            20                  25

<210> SEQ ID NO 19
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Gly Arg Lys Lys Arg Arg Gln Arg Arg Ala Arg Ser Arg Leu
1               5                   10                  15

Ala Glu Leu Arg Gly Val Pro Arg Phe Leu
            20                  25

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Gly Arg Lys Lys Arg Arg Gln Arg Arg Ala Arg Ser Arg Leu
1               5                   10                  15

Lys Glu Leu Arg Gly Val Pro Arg Phe Leu
            20                  25

<210> SEQ ID NO 21
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 21

Tyr Gly Arg Lys Lys Arg Arg Gln Arg Arg Ala Arg Ser Arg Leu
1               5                   10                  15

Ala Glu Leu Arg Gly Val Pro Arg Gly Leu
            20                  25

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

<400> SEQUENCE: 22

Tyr Gly Arg Lys Lys Arg Arg Gln Arg Arg Ala Arg Ser Arg Leu
1               5                   10                  15

```
Ala Glu Leu Arg Gly Val Pro Arg Gly Leu
            20                  25

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Gly Arg Lys Lys Arg Arg Gln Arg Arg Ala Arg Ser Arg Leu
1               5                   10                  15

Ala

<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Arg Lys Lys Arg Arg Gln Arg Arg Arg Pro Pro Gln Ala Arg Ser
1               5                   10                  15

Arg Leu Ala Glu Leu Arg Gly Val Pro Arg Gly Leu
            20                  25

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Arg Lys Lys Arg Arg Gln Arg Arg Arg Pro Pro Gln Ala Arg Ser
1               5                   10                  15

Arg Leu Lys Glu Leu Arg Gly Val Pro Arg Gly Leu
            20                  25

<210> SEQ ID NO 26
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Arg Lys Lys Arg Arg Gln Arg Arg Arg Pro Pro Gln Ala Arg Ser
1               5                   10                  15

Arg Leu Ala Glu Leu Leu Gly Val Pro Arg Gly Leu
            20                  25

<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 27

Gly Arg Lys Lys Arg Arg Gln Arg Arg Pro Pro Gln Ala Arg Ser
1               5                   10                  15

Arg Leu Ala Glu Leu Arg Gly Val Pro Arg Phe Leu
            20                  25

<210> SEQ ID NO 28
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 28

Gly Arg Lys Lys Arg Arg Gln Arg Arg Pro Pro Gln Ala Arg Ser
1               5                   10                  15

Arg Leu Ala Glu Leu Arg Gly Val Pro Arg Gly Leu
            20                  25

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

<400> SEQUENCE: 29

Gly Arg Lys Lys Arg Arg Gln Arg Arg Pro Pro Gln Ala Arg Ser
1               5                   10                  15

Arg Leu Ala Glu Leu Arg Gly Val Pro Arg Gly Leu
            20                  25

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Arg Lys Lys Arg Arg Gln Arg Arg Pro Pro Gln Ala Arg Ser
1               5                   10                  15

Arg Leu Ala

<210> SEQ ID NO 31
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Arg Gln Ile Lys Ile Trp Phe Gln Asn Arg Arg Met Lys Trp Lys Lys
1               5                   10                  15

Ala Arg Ser Arg Leu Ala Glu Leu Arg Gly Val Pro Arg Gly Leu
            20                  25                  30

```
<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Arg Gln Ile Lys Ile Trp Phe Gln Asn Arg Arg Met Lys Trp Lys Lys
1               5                   10                  15

Ala Arg Ser Arg Leu Lys Glu Leu Arg Gly Val Pro Arg Gly Leu
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Arg Gln Ile Lys Ile Trp Phe Gln Asn Arg Arg Met Lys Trp Lys Lys
1               5                   10                  15

Ala Arg Ser Arg Leu Ala Glu Leu Leu Gly Val Pro Arg Gly Leu
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Arg Gln Ile Lys Ile Trp Phe Gln Asn Arg Arg Met Lys Trp Lys Lys
1               5                   10                  15

Ala Arg Ser Arg Leu Ala Glu Leu Arg Gly Val Pro Arg Phe Leu
            20                  25                  30

<210> SEQ ID NO 35
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 35

Arg Gln Ile Lys Ile Trp Phe Gln Asn Arg Arg Met Lys Trp Lys Lys
1               5                   10                  15

Ala Arg Ser Arg Leu Ala Glu Leu Arg Gly Val Pro Arg Gly Leu
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<223> OTHER INFORMATION: N-term acetylated

<400> SEQUENCE: 36

Arg Gln Ile Lys Ile Trp Phe Gln Asn Arg Arg Met Lys Trp Lys Lys
1               5                   10                  15

Ala Arg Ser Arg Leu Ala Glu Leu Arg Gly Val Pro Arg Gly Leu
            20                  25                  30

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Gln Ile Lys Ile Trp Phe Gln Asn Arg Arg Met Lys Trp Lys Lys
1               5                   10                  15

Ala Arg Ser Arg Leu Ala
            20

<210> SEQ ID NO 38
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Leu Leu Ile Ile Leu Arg Arg Arg Ile Arg Lys Gln Ala His Ala His
1               5                   10                  15

Ser Lys Ala Arg Ser Arg Leu Ala Glu Leu Arg Gly Val Pro Arg Gly
            20                  25                  30

Leu

<210> SEQ ID NO 39
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Leu Leu Ile Ile Leu Arg Arg Arg Ile Arg Lys Gln Ala His Ala His
1               5                   10                  15

Ser Lys Ala Arg Ser Arg Leu Lys Glu Leu Arg Gly Val Pro Arg Gly
            20                  25                  30

Leu

<210> SEQ ID NO 40
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Leu Leu Ile Ile Leu Arg Arg Arg Ile Arg Lys Gln Ala His Ala His
1               5                   10                  15
```

```
Ser Lys Ala Arg Ser Arg Leu Ala Glu Leu Leu Gly Val Pro Arg Gly
            20                  25                  30

Leu

<210> SEQ ID NO 41
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Leu Leu Ile Ile Leu Arg Arg Arg Ile Arg Lys Gln Ala His Ala His
1               5                   10                  15

Ser Lys Ala Arg Ser Arg Leu Ala Glu Leu Arg Gly Val Pro Arg Phe
            20                  25                  30

Leu

<210> SEQ ID NO 42
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 42

Leu Leu Ile Ile Leu Arg Arg Arg Ile Arg Lys Gln Ala His Ala His
1               5                   10                  15

Ser Lys Ala Arg Ser Arg Leu Ala Glu Leu Arg Gly Val Pro Arg Gly
            20                  25                  30

Leu

<210> SEQ ID NO 43
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated

<400> SEQUENCE: 43

Leu Leu Ile Ile Leu Arg Arg Arg Ile Arg Lys Gln Ala His Ala His
1               5                   10                  15

Ser Lys Ala Arg Ser Arg Leu Ala Glu Leu Arg Gly Val Pro Arg Gly
            20                  25                  30

Leu

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Leu Ile Ile Leu Arg Arg Arg Ile Arg Lys Gln Ala His Ala His
1               5                   10                  15
```

Ser Lys Ala Arg Ser Arg Leu Ala
            20

<210> SEQ ID NO 45
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Arg Gly Gly Arg Leu Ser Tyr Ser Arg Arg Phe Ser Thr Ser Thr
1               5                   10                  15

Gly Arg Ala Arg Ser Arg Leu Ala Glu Leu Arg Gly Val Pro Arg Gly
            20                  25                  30

Leu

<210> SEQ ID NO 46
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Arg Gly Gly Arg Leu Ser Tyr Ser Arg Arg Phe Ser Thr Ser Thr
1               5                   10                  15

Gly Arg Ala Arg Ser Arg Leu Lys Glu Leu Arg Gly Val Pro Arg Gly
            20                  25                  30

Leu

<210> SEQ ID NO 47
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Arg Gly Gly Arg Leu Ser Tyr Ser Arg Arg Phe Ser Thr Ser Thr
1               5                   10                  15

Gly Arg Ala Arg Ser Arg Leu Ala Glu Leu Leu Gly Val Pro Arg Gly
            20                  25                  30

Leu

<210> SEQ ID NO 48
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Arg Gly Gly Arg Leu Ser Tyr Ser Arg Arg Phe Ser Thr Ser Thr
1               5                   10                  15

Gly Arg Ala Arg Ser Arg Leu Ala Glu Leu Arg Gly Val Pro Arg Phe
            20                  25                  30

Leu

<210> SEQ ID NO 49
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 49

Arg Gly Gly Arg Leu Ser Tyr Ser Arg Arg Phe Ser Thr Ser Thr
1               5                   10                  15

Gly Arg Ala Arg Ser Arg Leu Ala Glu Leu Arg Gly Val Pro Arg Gly
            20                  25                  30

Leu

<210> SEQ ID NO 50
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated

<400> SEQUENCE: 50

Arg Gly Gly Arg Leu Ser Tyr Ser Arg Arg Phe Ser Thr Ser Thr
1               5                   10                  15

Gly Arg Ala Arg Ser Arg Leu Ala Glu Leu Arg Gly Val Pro Arg Gly
            20                  25                  30

Leu

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Gly Gly Arg Leu Ser Tyr Ser Arg Arg Phe Ser Thr Ser Thr
1               5                   10                  15

Gly Arg Ala Arg Ser Arg Leu Ala
            20

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Arg Arg Arg Arg Arg Arg Arg Ala Arg Ser Arg Leu Ala Glu
1               5                   10                  15

Leu Arg Gly Val Pro Arg Gly Leu
            20

<210> SEQ ID NO 53

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Arg Arg Arg Arg Arg Arg Arg Arg Ala Arg Ser Arg Leu Lys Glu
1               5                   10                  15

Leu Arg Gly Val Pro Arg Gly Leu
            20

<210> SEQ ID NO 54
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Arg Arg Arg Arg Arg Arg Arg Arg Ala Arg Ser Arg Leu Ala Glu
1               5                   10                  15

Leu Leu Gly Val Pro Arg Gly Leu
            20

<210> SEQ ID NO 55
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Arg Arg Arg Arg Arg Arg Arg Arg Ala Arg Ser Arg Leu Ala Glu
1               5                   10                  15

Leu Arg Gly Val Pro Arg Phe Leu
            20

<210> SEQ ID NO 56
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 56

Arg Arg Arg Arg Arg Arg Arg Arg Arg Ala Arg Ser Arg Leu Ala Glu
1               5                   10                  15

Leu Arg Gly Val Pro Arg Gly Leu
            20

<210> SEQ ID NO 57
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
```

<400> SEQUENCE: 57

Arg Arg Arg Arg Arg Arg Arg Arg Ala Arg Ser Arg Leu Ala Glu
1               5                   10                  15

Leu Arg Gly Val Pro Arg Gly Leu
            20

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Arg Arg Arg Arg Arg Arg Arg Ala Arg Ser Arg Leu Ala
1               5                   10                  15

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Arg Arg Arg Arg Arg Arg Arg Arg Pro Pro Gln Ala Arg Ser
1               5                   10                  15

Arg Leu Ala Glu Leu Arg Gly Val Pro Arg Gly Leu
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Arg Arg Arg Arg Arg Arg Arg Arg Pro Pro Gln Ala Arg Ser
1               5                   10                  15

Arg Leu Lys Glu Leu Arg Gly Val Pro Arg Gly Leu
            20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Arg Arg Arg Arg Arg Arg Arg Arg Pro Pro Gln Ala Arg Ser
1               5                   10                  15

Arg Leu Ala Glu Leu Leu Gly Val Pro Arg Gly Leu
            20                  25

<210> SEQ ID NO 62
<211> LENGTH: 28
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 62

Gly Arg Arg Arg Arg Arg Arg Arg Arg Pro Pro Gln Ala Arg Ser
1               5                   10                  15

Arg Leu Ala Glu Leu Arg Gly Val Pro Arg Phe Leu
            20                  25

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 63

Gly Arg Arg Arg Arg Arg Arg Arg Arg Pro Pro Gln Ala Arg Ser
1               5                   10                  15

Arg Leu Ala Glu Leu Arg Gly Val Pro Arg Gly Leu
            20                  25

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

<400> SEQUENCE: 64

Gly Arg Arg Arg Arg Arg Arg Arg Arg Pro Pro Gln Ala Arg Ser
1               5                   10                  15

Arg Leu Ala Glu Leu Arg Gly Val Pro Arg Gly Leu
            20                  25

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Arg Arg Arg Arg Arg Arg Arg Arg Pro Pro Gln Ala Arg Ser
1               5                   10                  15

Arg Leu Ala

<210> SEQ ID NO 66
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ala Ala Val Ala Leu Leu Pro Ala Val Leu Leu Ala Leu Leu Ala Pro
1               5                   10                  15
```

Ala Arg Ser Arg Leu Ala Glu Leu Arg Gly Val Pro Arg Gly Leu
            20                  25                  30

<210> SEQ ID NO 67
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Ala Val Ala Leu Leu Pro Ala Val Leu Leu Ala Leu Leu Ala Pro
1               5                   10                  15

Ala Arg Ser Arg Leu Lys Glu Leu Arg Gly Val Pro Arg Gly Leu
            20                  25                  30

<210> SEQ ID NO 68
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Ala Val Ala Leu Leu Pro Ala Val Leu Leu Ala Leu Leu Ala Pro
1               5                   10                  15

Ala Arg Ser Arg Leu Ala Glu Leu Leu Gly Val Pro Arg Gly Leu
            20                  25                  30

<210> SEQ ID NO 69
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Ala Val Ala Leu Leu Pro Ala Val Leu Leu Ala Leu Leu Ala Pro
1               5                   10                  15

Ala Arg Ser Arg Leu Ala Glu Leu Arg Gly Val Pro Arg Phe Leu
            20                  25                  30

<210> SEQ ID NO 70
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 70

Ala Ala Val Ala Leu Leu Pro Ala Val Leu Leu Ala Leu Leu Ala Pro
1               5                   10                  15

Ala Arg Ser Arg Leu Ala Glu Leu Arg Gly Val Pro Arg Gly Leu
            20                  25                  30

<210> SEQ ID NO 71
<211> LENGTH: 31
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<223> OTHER INFORMATION: N-term acetylated

<400> SEQUENCE: 71

Ala Ala Val Ala Leu Leu Pro Ala Val Leu Leu Ala Leu Leu Ala Pro
1               5                  10                  15

Ala Arg Ser Arg Leu Ala Glu Leu Arg Gly Val Pro Arg Gly Leu
            20                  25                  30

<210> SEQ ID NO 72
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Ala Val Ala Leu Leu Pro Ala Val Leu Leu Ala Leu Leu Ala Pro
1               5                  10                  15

Ala Arg Ser Arg Leu Ala
            20

<210> SEQ ID NO 73
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Leu Ser Ser Ile Phe Ser Arg Ile Gly Asp Pro Ala Arg Ser Arg
1               5                  10                  15

Leu Ala Glu Leu Arg Gly Val Pro Arg Gly Leu
            20                  25

<210> SEQ ID NO 74
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Leu Ser Ser Ile Phe Ser Arg Ile Gly Asp Pro Ala Arg Ser Arg
1               5                  10                  15

Leu Lys Glu Leu Arg Gly Val Pro Arg Gly Leu
            20                  25

<210> SEQ ID NO 75
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Leu Ser Ser Ile Phe Ser Arg Ile Gly Asp Pro Ala Arg Ser Arg
1               5                  10                  15

Leu Ala Glu Leu Leu Gly Val Pro Arg Gly Leu
```

```
            20                  25

<210> SEQ ID NO 76
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Pro Leu Ser Ser Ile Phe Ser Arg Ile Gly Asp Pro Ala Arg Ser Arg
1               5                   10                  15

Leu Ala Glu Leu Arg Gly Val Pro Arg Phe Leu
            20                  25

<210> SEQ ID NO 77
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 77

Pro Leu Ser Ser Ile Phe Ser Arg Ile Gly Asp Pro Ala Arg Ser Arg
1               5                   10                  15

Leu Ala Glu Leu Arg Gly Val Pro Arg Gly Leu
            20                  25

<210> SEQ ID NO 78
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

<400> SEQUENCE: 78

Pro Leu Ser Ser Ile Phe Ser Arg Ile Gly Asp Pro Ala Arg Ser Arg
1               5                   10                  15

Leu Ala Glu Leu Arg Gly Val Pro Arg Gly Leu
            20                  25

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Pro Leu Ser Ser Ile Phe Ser Arg Ile Gly Asp Pro Ala Arg Ser Arg
1               5                   10                  15

Leu Ala

<210> SEQ ID NO 80
<211> LENGTH: 28
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 80

Thr Arg Arg Gln Arg Thr Arg Arg Ala Arg Arg Asn Arg Ala Arg Ser
1               5                   10                  15

Arg Leu Ala Glu Leu Arg Gly Val Pro Arg Gly Leu
            20                  25

<210> SEQ ID NO 81
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Arg Arg Gln Arg Thr Arg Arg Ala Arg Arg Asn Arg Ala Arg Ser
1               5                   10                  15

Arg Leu Lys Glu Leu Arg Gly Val Pro Arg Gly Leu
            20                  25

<210> SEQ ID NO 82
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Arg Arg Gln Arg Thr Arg Arg Ala Arg Arg Asn Arg Ala Arg Ser
1               5                   10                  15

Arg Leu Ala Glu Leu Leu Gly Val Pro Arg Gly Leu
            20                  25

<210> SEQ ID NO 83
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Arg Arg Gln Arg Thr Arg Arg Ala Arg Arg Asn Arg Ala Arg Ser
1               5                   10                  15

Arg Leu Ala Glu Leu Arg Gly Val Pro Arg Phe Leu
            20                  25

<210> SEQ ID NO 84
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 84

Thr Arg Arg Gln Arg Thr Arg Arg Ala Arg Arg Asn Arg Ala Arg Ser
1               5                   10                  15

Arg Leu Ala Glu Leu Arg Gly Val Pro Arg Gly Leu
```

```
            20                  25

<210> SEQ ID NO 85
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

<400> SEQUENCE: 85

Thr Arg Arg Gln Arg Thr Arg Arg Ala Arg Arg Asn Arg Ala Arg Ser
1               5                   10                  15

Arg Leu Ala Glu Leu Arg Gly Val Pro Arg Gly Leu
            20                  25

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Arg Arg Gln Arg Thr Arg Arg Ala Arg Arg Asn Arg Ala Arg Ser
1               5                   10                  15

Arg Leu Ala

<210> SEQ ID NO 87
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Lys Leu Ala Leu Lys Leu Ala Leu Lys Ala Leu Lys Ala Ala Leu Lys
1               5                   10                  15

Leu Ala Ala Arg Ser Arg Leu Ala Glu Leu Arg Gly Val Pro Arg Gly
            20                  25                  30

Leu

<210> SEQ ID NO 88
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Lys Leu Ala Leu Lys Leu Ala Leu Lys Ala Leu Lys Ala Ala Leu Lys
1               5                   10                  15

Leu Ala Ala Arg Ser Arg Leu Lys Glu Leu Arg Gly Val Pro Arg Gly
            20                  25                  30

Leu

<210> SEQ ID NO 89
<211> LENGTH: 33
<212> TYPE: PRT
```

<213> ORGANISM: Artificial Sequence
<220> FEATURE:
<223> OTHER INFORMATION: Description of Artificial Sequence: Synthetic
     polypeptide

<400> SEQUENCE: 89

Lys Leu Ala Leu Lys Leu Ala Leu Lys Ala Leu Lys Ala Ala Leu Lys
1               5                   10                  15

Leu Ala Ala Arg Ser Arg Leu Ala Glu Leu Leu Gly Val Pro Arg Gly
            20                  25                  30

Leu

<210> SEQ ID NO 90
<211> LENGTH: 33
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 90

Lys Leu Ala Leu Lys Leu Ala Leu Lys Ala Leu Lys Ala Ala Leu Lys
1               5                   10                  15

Leu Ala Ala Arg Ser Arg Leu Ala Glu Leu Arg Gly Val Pro Arg Phe
            20                  25                  30

Leu

<210> SEQ ID NO 91
<211> LENGTH: 33
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: C-term amidated

<400> SEQUENCE: 91

Lys Leu Ala Leu Lys Leu Ala Leu Lys Ala Leu Lys Ala Ala Leu Lys
1               5                   10                  15

Leu Ala Ala Arg Ser Arg Leu Ala Glu Leu Arg Gly Val Pro Arg Gly
            20                  25                  30

Leu

<210> SEQ ID NO 92
<211> LENGTH: 33
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: N-term acetylated

<400> SEQUENCE: 92

Lys Leu Ala Leu Lys Leu Ala Leu Lys Ala Leu Lys Ala Ala Leu Lys
1               5                   10                  15

Leu Ala Ala Arg Ser Arg Leu Ala Glu Leu Arg Gly Val Pro Arg Gly
            20                  25                  30

Leu

<210> SEQ ID NO 93
<211> LENGTH: 24

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Leu Ala Leu Lys Leu Ala Leu Lys Ala Leu Lys Ala Ala Leu Lys
1               5                   10                  15

Leu Ala Ala Arg Ser Arg Leu Ala
            20

<210> SEQ ID NO 94
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ala Gly Tyr Leu Leu Gly Lys Ile Asn Leu Lys Ala Leu Ala Ala Leu
1               5                   10                  15

Ala Lys Lys Ile Leu Ala Arg Ser Arg Leu Ala Glu Leu Arg Gly Val
            20                  25                  30

Pro Arg Gly Leu
        35

<210> SEQ ID NO 95
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Gly Tyr Leu Leu Gly Lys Ile Asn Leu Lys Ala Leu Ala Ala Leu
1               5                   10                  15

Ala Lys Lys Ile Leu Ala Arg Ser Arg Leu Lys Glu Leu Arg Gly Val
            20                  25                  30

Pro Arg Gly Leu
        35

<210> SEQ ID NO 96
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ala Gly Tyr Leu Leu Gly Lys Ile Asn Leu Lys Ala Leu Ala Ala Leu
1               5                   10                  15

Ala Lys Lys Ile Leu Ala Arg Ser Arg Leu Ala Glu Leu Leu Gly Val
            20                  25                  30

Pro Arg Gly Leu
        35

<210> SEQ ID NO 97
<211> LENGTH: 36
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 97

Ala Gly Tyr Leu Leu Gly Lys Ile Asn Leu Lys Ala Leu Ala Ala Leu
1               5                   10                  15

Ala Lys Lys Ile Leu Ala Arg Ser Arg Leu Ala Glu Leu Arg Gly Val
            20                  25                  30

Pro Arg Phe Leu
        35

<210> SEQ ID NO 98
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 98

Ala Gly Tyr Leu Leu Gly Lys Ile Asn Leu Lys Ala Leu Ala Ala Leu
1               5                   10                  15

Ala Lys Lys Ile Leu Ala Arg Ser Arg Leu Ala Glu Leu Arg Gly Val
            20                  25                  30

Pro Arg Gly Leu
        35

<210> SEQ ID NO 99
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated

<400> SEQUENCE: 99

Ala Gly Tyr Leu Leu Gly Lys Ile Asn Leu Lys Ala Leu Ala Ala Leu
1               5                   10                  15

Ala Lys Lys Ile Leu Ala Arg Ser Arg Leu Ala Glu Leu Arg Gly Val
            20                  25                  30

Pro Arg Gly Leu
        35

<210> SEQ ID NO 100
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Gly Tyr Leu Leu Gly Lys Ile Asn Leu Lys Ala Leu Ala Ala Leu
1               5                   10                  15

Ala Lys Lys Ile Leu Ala Arg Ser Arg Leu Ala
            20                  25

<210> SEQ ID NO 101
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Lys Glu Thr Trp Trp Glu Thr Trp Trp Thr Glu Trp Ser Gln Pro Lys
1               5                   10                  15

Lys Lys Arg Lys Val Ala Arg Ser Arg Leu Ala Glu Leu Arg Gly Val
            20                  25                  30

Pro Arg Gly Leu
        35

<210> SEQ ID NO 102
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Lys Glu Thr Trp Trp Glu Thr Trp Trp Thr Glu Trp Ser Gln Pro Lys
1               5                   10                  15

Lys Lys Arg Lys Val Ala Arg Ser Arg Leu Lys Glu Leu Arg Gly Val
            20                  25                  30

Pro Arg Gly Leu
        35

<210> SEQ ID NO 103
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Lys Glu Thr Trp Trp Glu Thr Trp Trp Thr Glu Trp Ser Gln Pro Lys
1               5                   10                  15

Lys Lys Arg Lys Val Ala Arg Ser Arg Leu Ala Glu Leu Leu Gly Val
            20                  25                  30

Pro Arg Gly Leu
        35

<210> SEQ ID NO 104
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Lys Glu Thr Trp Trp Glu Thr Trp Trp Thr Glu Trp Ser Gln Pro Lys
1               5                   10                  15

Lys Lys Arg Lys Val Ala Arg Ser Arg Leu Ala Glu Leu Arg Gly Val
            20                  25                  30

Pro Arg Phe Leu
        35

<210> SEQ ID NO 105
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 105

Lys Glu Thr Trp Trp Glu Thr Trp Trp Thr Glu Trp Ser Gln Pro Lys
1               5                   10                  15

Lys Lys Arg Lys Val Ala Arg Ser Arg Leu Ala Glu Leu Arg Gly Val
            20                  25                  30

Pro Arg Gly Leu
        35

<210> SEQ ID NO 106
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated

<400> SEQUENCE: 106

Lys Glu Thr Trp Trp Glu Thr Trp Trp Thr Glu Trp Ser Gln Pro Lys
1               5                   10                  15

Lys Lys Arg Lys Val Ala Arg Ser Arg Leu Ala Glu Leu Arg Gly Val
            20                  25                  30

Pro Arg Gly Leu
        35

<210> SEQ ID NO 107
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Lys Glu Thr Trp Trp Glu Thr Trp Trp Thr Glu Trp Ser Gln Pro Lys
1               5                   10                  15

Lys Lys Arg Lys Val Ala Arg Ser Arg Leu Ala
            20                  25

<210> SEQ ID NO 108
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Ala Leu Asn Leu Gly Trp Leu Leu Ala Leu Phe Val Thr Met Trp
1               5                   10                  15

Thr Asp Val Gly Leu Cys Lys Lys Arg Pro Lys Pro Ala Arg Ser Arg
            20                  25                  30

Leu Ala Glu Leu Arg Gly Val Pro Arg Gly Leu
        35                  40
```

<210> SEQ ID NO 109
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Ala Leu Asn Leu Gly Trp Leu Leu Ala Leu Phe Val Thr Met Trp
1               5                   10                  15

Thr Asp Val Gly Leu Cys Lys Lys Arg Pro Lys Pro Ala Arg Ser Arg
                20                  25                  30

Leu Lys Glu Leu Arg Gly Val Pro Arg Gly Leu
            35                  40

<210> SEQ ID NO 110
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Met Ala Leu Asn Leu Gly Trp Leu Leu Ala Leu Phe Val Thr Met Trp
1               5                   10                  15

Thr Asp Val Gly Leu Cys Lys Lys Arg Pro Lys Pro Ala Arg Ser Arg
                20                  25                  30

Leu Ala Glu Leu Leu Gly Val Pro Arg Gly Leu
            35                  40

<210> SEQ ID NO 111
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Ala Leu Asn Leu Gly Trp Leu Leu Ala Leu Phe Val Thr Met Trp
1               5                   10                  15

Thr Asp Val Gly Leu Cys Lys Lys Arg Pro Lys Pro Ala Arg Ser Arg
                20                  25                  30

Leu Ala Glu Leu Arg Gly Val Pro Arg Phe Leu
            35                  40

<210> SEQ ID NO 112
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 112

Met Ala Leu Asn Leu Gly Trp Leu Leu Ala Leu Phe Val Thr Met Trp
1               5                   10                  15

Thr Asp Val Gly Leu Cys Lys Lys Arg Pro Lys Pro Ala Arg Ser Arg
                20                  25                  30

```
Leu Ala Glu Leu Arg Gly Val Pro Arg Gly Leu
        35                  40
```

<210> SEQ ID NO 113
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated

<400> SEQUENCE: 113

```
Met Ala Leu Asn Leu Gly Trp Leu Leu Ala Leu Phe Val Thr Met Trp
1               5                   10                  15

Thr Asp Val Gly Leu Cys Lys Lys Arg Pro Lys Pro Ala Arg Ser Arg
            20                  25                  30

Leu Ala Glu Leu Arg Gly Val Pro Arg Gly Leu
        35                  40
```

<210> SEQ ID NO 114
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Met Ala Leu Asn Leu Gly Trp Leu Leu Ala Leu Phe Val Thr Met Trp
1               5                   10                  15

Thr Asp Val Gly Leu Cys Lys Lys Arg Pro Lys Pro Ala Arg Ser Arg
            20                  25                  30

Leu Ala
```

<210> SEQ ID NO 115
<211> LENGTH: 19
<212> TYPE: PRT
<213> ORGANISM: Homo sapiens

<400> SEQUENCE: 115

```
Asn Gly Tyr Leu Glu Trp Ile Phe Lys Ala Glu Glu Val Met Leu Ala
1               5                   10                  15

Glu Glu Asp
```

<210> SEQ ID NO 116
<211> LENGTH: 19
<212> TYPE: PRT
<213> ORGANISM: Homo sapiens

<400> SEQUENCE: 116

```
Asn Gly Tyr Met Glu Trp Ile Ser Lys Ala Glu Glu Val Ile Leu Ala
1               5                   10                  15

Glu Asp Glu
```

<210> SEQ ID NO 117
<211> LENGTH: 19
<212> TYPE: PRT
<213> ORGANISM: Homo sapiens

<400> SEQUENCE: 117

```
Asn Gly Tyr Arg Ala Trp Ile Asp Lys Ala Glu Glu Val Met Leu Ala
```

-continued

```
                1               5                  10                  15

Glu Glu Asn

<210> SEQ ID NO 118
<211> LENGTH: 19
<212> TYPE: PRT
<213> ORGANISM: Homo sapiens

<400> SEQUENCE: 118

Lys Gly Tyr Leu Asp Trp Ile Thr Gln Ala Glu Asp Ile Asp Pro Glu
1               5                   10                  15

Asn Glu Asp

<210> SEQ ID NO 119
<211> LENGTH: 29
<212> TYPE: PRT
<213> ORGANISM: Rattus norvegicus

<400> SEQUENCE: 119

Ala Glu Ser Ser Glu Lys Leu Asn Ser Ser Phe Pro Ser Ile His Cys
1               5                   10                  15

Ser Ser Trp Ser Glu Glu Thr Thr Ala Cys Ser Gly Gly
            20                  25

<210> SEQ ID NO 120
<211> LENGTH: 23
<212> TYPE: PRT
<213> ORGANISM: Rattus norvegicus

<400> SEQUENCE: 120

Ser Ile Thr Tyr Lys Thr Ala Asn Ser Ser Pro Val His Phe Ala Glu
1               5                   10                  15

Gly Gln Ser Gly Leu Pro Ala
            20

<210> SEQ ID NO 121
<211> LENGTH: 20
<212> TYPE: PRT
<213> ORGANISM: Rattus norvegicus

<400> SEQUENCE: 121

Leu Val Ser Tyr Ser Pro Ala Pro Arg Arg Pro Ala Ala Arg Arg Met
1               5                   10                  15

Ala Gly Pro Pro
            20

<210> SEQ ID NO 122
<211> LENGTH: 27
<212> TYPE: PRT
<213> ORGANISM: Rattus norvegicus

<400> SEQUENCE: 122

Leu Leu Ser Tyr Ser Ser Leu Met Arg His Thr Gly Gly Ile Ser Pro
1               5                   10                  15

Pro Pro Asp Gly Ser Glu Gly Gly Ser Pro Leu
            20                  25

<210> SEQ ID NO 123
<211> LENGTH: 10
<212> TYPE: PRT
<213> ORGANISM: Homo sapiens
<220> FEATURE:
```

```
<221> NAME/KEY: MOD_RES
<222> LOCATION: (7)..(7)
<223> OTHER INFORMATION: Any optionally substituted amino acid
<220> FEATURE:
<221> NAME/KEY: MOD_RES
<222> LOCATION: (9)..(9)
<223> OTHER INFORMATION: Any optionally substituted amino acid

<400> SEQUENCE: 123

Ala Arg Ser Arg Leu Ala Xaa Leu Xaa Gly
1               5                   10

<210> SEQ ID NO 124
<211> LENGTH: 15
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any optionally substituted amino acid
<220> FEATURE:
<221> NAME/KEY: MOD_RES
<222> LOCATION: (6)..(7)
<223> OTHER INFORMATION: Any optionally substituted amino acid
<220> FEATURE:
<221> NAME/KEY: MOD_RES
<222> LOCATION: (10)..(15)
<223> OTHER INFORMATION: Any optionally substituted amino acid

<400> SEQUENCE: 124

Tyr Xaa Xaa Trp Ile Xaa Xaa Ala Glu Xaa Xaa Xaa Xaa Xaa Xaa
1               5                   10                  15

<210> SEQ ID NO 125
<211> LENGTH: 15
<212> TYPE: PRT
<213> ORGANISM: Homo sapiens

<400> SEQUENCE: 125

Tyr Leu Glu Trp Ile Phe Lys Ala Glu Glu Val Met Leu Ala Glu
1               5                   10                  15

<210> SEQ ID NO 126
<211> LENGTH: 15
<212> TYPE: PRT
<213> ORGANISM: Rattus norvegicus
<220> FEATURE:
<221> NAME/KEY: MOD_RES
<222> LOCATION: (4)..(15)
<223> OTHER INFORMATION: Any optionally substituted amino acid

<400> SEQUENCE: 126

Asn Ser Ser Xaa Xaa Xaa Xaa Xaa Xaa Xaa Xaa Xaa Xaa Xaa Xaa
1               5                   10                  15

<210> SEQ ID NO 127
<211> LENGTH: 15
<212> TYPE: PRT
<213> ORGANISM: Rattus norvegicus

<400> SEQUENCE: 127

Asn Ser Ser Phe Pro Ser Ile His Cys Ser Ser Trp Ser Glu Glu
1               5                   10                  15

<210> SEQ ID NO 128
<211> LENGTH: 4
<212> TYPE: PRT
<213> ORGANISM: Homo sapiens
```

```
<400> SEQUENCE: 128

Ala Arg Ser Arg
1

<210> SEQ ID NO 129
<211> LENGTH: 5
<212> TYPE: PRT
<213> ORGANISM: Homo sapiens

<400> SEQUENCE: 129

Ala Arg Ser Arg Leu
1               5

<210> SEQ ID NO 130
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Any amino acid

<400> SEQUENCE: 130

Ala Arg Ser Arg Leu Xaa
1               5

<210> SEQ ID NO 131
<211> LENGTH: 6
<212> TYPE: PRT
<213> ORGANISM: Homo sapiens

<400> SEQUENCE: 131

Ala Arg Ser Arg Leu Lys
1               5

<210> SEQ ID NO 132
<211> LENGTH: 9
<212> TYPE: PRT
<213> ORGANISM: Homo sapiens
<220> FEATURE:
<221> NAME/KEY: MOD_RES
<222> LOCATION: (5)..(8)
<223> OTHER INFORMATION: Any optionally substituted amino acid

<400> SEQUENCE: 132

Ala Arg Ser Arg Xaa Xaa Xaa Xaa Leu
1               5

<210> SEQ ID NO 133
<211> LENGTH: 9
<212> TYPE: PRT
<213> ORGANISM: Homo sapiens
<220> FEATURE:
<221> NAME/KEY: MOD_RES
<222> LOCATION: (6)..(8)
<223> OTHER INFORMATION: Any optionally substituted amino acid

<400> SEQUENCE: 133

Ala Arg Ser Arg Leu Xaa Xaa Xaa Leu
1               5

<210> SEQ ID NO 134
<211> LENGTH: 9
<212> TYPE: PRT
<213> ORGANISM: Homo sapiens
<220> FEATURE:
<221> NAME/KEY: MOD_RES
```

```
<222> LOCATION: (7)..(8)
<223> OTHER INFORMATION: Any optionally substituted amino acid

<400> SEQUENCE: 134

Ala Arg Ser Arg Leu Ala Xaa Xaa Leu
1               5

<210> SEQ ID NO 135
<211> LENGTH: 12
<212> TYPE: PRT
<213> ORGANISM: Homo sapiens
<220> FEATURE:
<221> NAME/KEY: MOD_RES
<222> LOCATION: (5)..(10)
<223> OTHER INFORMATION: Any optionally substituted amino acid

<400> SEQUENCE: 135

Ala Arg Ser Arg Xaa Xaa Xaa Xaa Xaa Xaa Val Pro
1               5                   10

<210> SEQ ID NO 136
<211> LENGTH: 12
<212> TYPE: PRT
<213> ORGANISM: Homo sapiens
<220> FEATURE:
<221> NAME/KEY: MOD_RES
<222> LOCATION: (6)..(10)
<223> OTHER INFORMATION: Any optionally substituted amino acid

<400> SEQUENCE: 136

Ala Arg Ser Arg Leu Xaa Xaa Xaa Xaa Xaa Val Pro
1               5                   10

<210> SEQ ID NO 137
<211> LENGTH: 12
<212> TYPE: PRT
<213> ORGANISM: Homo sapiens
<220> FEATURE:
<221> NAME/KEY: MOD_RES
<222> LOCATION: (7)..(10)
<223> OTHER INFORMATION: Any optionally substituted amino acid

<400> SEQUENCE: 137

Ala Arg Ser Arg Leu Ala Xaa Xaa Xaa Xaa Val Pro
1               5                   10

<210> SEQ ID NO 138
<211> LENGTH: 13
<212> TYPE: PRT
<213> ORGANISM: Homo sapiens
<220> FEATURE:
<221> NAME/KEY: MOD_RES
<222> LOCATION: (5)..(10)
<223> OTHER INFORMATION: Any optionally substituted amino acid

<400> SEQUENCE: 138

Ala Arg Ser Arg Xaa Xaa Xaa Xaa Xaa Xaa Val Pro Arg
1               5                   10

<210> SEQ ID NO 139
<211> LENGTH: 13
<212> TYPE: PRT
<213> ORGANISM: Homo sapiens
<220> FEATURE:
<221> NAME/KEY: MOD_RES
<222> LOCATION: (6)..(10)
<223> OTHER INFORMATION: Any optionally substituted amino acid

<400> SEQUENCE: 139
```

```
Ala Arg Ser Arg Leu Xaa Xaa Xaa Xaa Val Pro Arg
1               5                   10
```

<210> SEQ ID NO 140
<211> LENGTH: 13
<212> TYPE: PRT
<213> ORGANISM: Homo sapiens
<220> FEATURE:
<221> NAME/KEY: MOD_RES
<222> LOCATION: (7)..(10)
<223> OTHER INFORMATION: Any optionally substituted amino acid

<400> SEQUENCE: 140

```
Ala Arg Ser Arg Leu Ala Xaa Xaa Xaa Xaa Val Pro Arg
1               5                   10
```

<210> SEQ ID NO 141
<211> LENGTH: 14
<212> TYPE: PRT
<213> ORGANISM: Homo sapiens
<220> FEATURE:
<221> NAME/KEY: MOD_RES
<222> LOCATION: (5)..(13)
<223> OTHER INFORMATION: Any optionally substituted amino acid

<400> SEQUENCE: 141

```
Ala Arg Ser Arg Xaa Xaa Xaa Xaa Xaa Xaa Xaa Xaa Xaa Phe
1               5                   10
```

<210> SEQ ID NO 142
<211> LENGTH: 14
<212> TYPE: PRT
<213> ORGANISM: Homo sapiens
<220> FEATURE:
<221> NAME/KEY: MOD_RES
<222> LOCATION: (6)..(13)
<223> OTHER INFORMATION: Any optionally substituted amino acid

<400> SEQUENCE: 142

```
Ala Arg Ser Arg Leu Xaa Xaa Xaa Xaa Xaa Xaa Xaa Xaa Phe
1               5                   10
```

<210> SEQ ID NO 143
<211> LENGTH: 14
<212> TYPE: PRT
<213> ORGANISM: Homo sapiens
<220> FEATURE:
<221> NAME/KEY: MOD_RES
<222> LOCATION: (7)..(13)
<223> OTHER INFORMATION: Any optionally substituted amino acid

<400> SEQUENCE: 143

```
Ala Arg Ser Arg Leu Ala Xaa Xaa Xaa Xaa Xaa Xaa Xaa Phe
1               5                   10
```

<210> SEQ ID NO 144
<211> LENGTH: 15
<212> TYPE: PRT
<213> ORGANISM: Homo sapiens
<220> FEATURE:
<221> NAME/KEY: MOD_RES
<222> LOCATION: (5)..(10)
<223> OTHER INFORMATION: Any optionally substituted amino acid
<220> FEATURE:
<221> NAME/KEY: MOD_RES
<222> LOCATION: (14)..(14)
<223> OTHER INFORMATION: Any optionally substituted amino acid

<400> SEQUENCE: 144

```
Ala Arg Ser Arg Xaa Xaa Xaa Xaa Xaa Val Pro Arg Xaa Leu
1               5                   10                  15
```

<210> SEQ ID NO 145
<211> LENGTH: 15
<212> TYPE: PRT
<213> ORGANISM: Homo sapiens
<220> FEATURE:
<221> NAME/KEY: MOD_RES
<222> LOCATION: (6)..(10)
<223> OTHER INFORMATION: Any optionally substituted amino acid
<220> FEATURE:
<221> NAME/KEY: MOD_RES
<222> LOCATION: (14)..(14)
<223> OTHER INFORMATION: Any optionally substituted amino acid

<400> SEQUENCE: 145

```
Ala Arg Ser Arg Leu Xaa Xaa Xaa Xaa Xaa Val Pro Arg Xaa Leu
1               5                   10                  15
```

<210> SEQ ID NO 146
<211> LENGTH: 15
<212> TYPE: PRT
<213> ORGANISM: Homo sapiens
<220> FEATURE:
<221> NAME/KEY: MOD_RES
<222> LOCATION: (7)..(10)
<223> OTHER INFORMATION: Any optionally substituted amino acid
<220> FEATURE:
<221> NAME/KEY: MOD_RES
<222> LOCATION: (14)..(14)
<223> OTHER INFORMATION: Any optionally substituted amino acid

<400> SEQUENCE: 146

```
Ala Arg Ser Arg Leu Ala Xaa Xaa Xaa Xaa Val Pro Arg Xaa Leu
1               5                   10                  15
```

<210> SEQ ID NO 147
<211> LENGTH: 10
<212> TYPE: PRT
<213> ORGANISM: Homo sapiens
<220> FEATURE:
<221> NAME/KEY: MOD_RES
<222> LOCATION: (5)..(7)
<223> OTHER INFORMATION: Any optionally substituted amino acid
<220> FEATURE:
<221> NAME/KEY: MOD_RES
<222> LOCATION: (9)..(9)
<223> OTHER INFORMATION: Any optionally substituted amino acid

<400> SEQUENCE: 147

```
Ala Arg Ser Arg Xaa Xaa Xaa Leu Xaa Gly
1               5                   10
```

<210> SEQ ID NO 148
<211> LENGTH: 10
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Any optionally substituted amino acid
<220> FEATURE:
<221> NAME/KEY: MOD_RES
<222> LOCATION: (9)..(9)
<223> OTHER INFORMATION: Any optionally substituted amino acid

<400> SEQUENCE: 148

```
Ala Arg Ser Arg Leu Xaa Xaa Leu Xaa Gly
1               5                   10
```

```
<210> SEQ ID NO 149
<211> LENGTH: 15
<212> TYPE: PRT
<213> ORGANISM: Homo sapiens

<400> SEQUENCE: 149

Tyr Met Glu Trp Ile Ser Lys Ala Glu Glu Val Ile Leu Ala Glu
1               5                   10                  15

<210> SEQ ID NO 150
<211> LENGTH: 15
<212> TYPE: PRT
<213> ORGANISM: Homo sapiens

<400> SEQUENCE: 150

Tyr Arg Ala Trp Ile Asp Lys Ala Glu Glu Val Met Leu Ala Glu
1               5                   10                  15

<210> SEQ ID NO 151
<211> LENGTH: 15
<212> TYPE: PRT
<213> ORGANISM: Homo sapiens

<400> SEQUENCE: 151

Tyr Leu Asp Trp Ile Thr Gln Ala Glu Asp Ile Asp Pro Glu Asn
1               5                   10                  15

<210> SEQ ID NO 152
<211> LENGTH: 9
<212> TYPE: PRT
<213> ORGANISM: Rattus norvegicus

<400> SEQUENCE: 152

Asn Ser Ser Pro Val His Phe Ala Glu
1               5

<210> SEQ ID NO 153
<211> LENGTH: 6
<212> TYPE: PRT
<213> ORGANISM: Rattus norvegicus

<400> SEQUENCE: 153

Pro Arg Arg Pro Ala Ala
1               5

<210> SEQ ID NO 154
<211> LENGTH: 13
<212> TYPE: PRT
<213> ORGANISM: Rattus norvegicus

<400> SEQUENCE: 154

Met Arg His Thr Gly Gly Ile Ser Pro Pro Asp Gly
1               5                   10
```